(12) United States Patent
Danesh et al.

(10) Patent No.: US 12,714,351 B2
(45) Date of Patent: Aug. 25, 2026

(54) HIGH RESOLUTION ELECTROENCEPHALOGRAPH SIGNAL ACQUISITION SYSTEM

(71) Applicant: THE REGENTS OF THE UNIVERSITY OF CALIFORNIA, Oakland, CA (US)

(72) Inventors: Ahmadreza Danesh, Irvine, CA (US); Payam Heydari, Irvine, CA (US); Haoran Pu, Irvine, CA (US); Zoran Nenadic, Irvine, CA (US); An H. Do, Irvine, CA (US); Omid Malekzadeh Arasteh, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 409 days.

(21) Appl. No.: 18/245,120

(22) PCT Filed: Dec. 9, 2021

(86) PCT No.: PCT/US2021/062602
§ 371 (c)(1),
(2) Date: Mar. 13, 2023

(87) PCT Pub. No.: WO2022/125773
PCT Pub. Date: Jun. 16, 2022

(65) Prior Publication Data

US 2023/0355156 A1 Nov. 9, 2023

Related U.S. Application Data

(60) Provisional application No. 63/123,160, filed on Dec. 9, 2020.

(51) Int. Cl.
*A61B 5/31* (2021.01)
*A61B 5/369* (2021.01)

(52) U.S. Cl.
CPC ................ *A61B 5/31* (2021.01); *A61B 5/369* (2021.01)

(58) Field of Classification Search
CPC ............ A61B 5/31; A61B 5/369; A61B 5/291
See application file for complete search history.

(56) References Cited

U.S. PATENT DOCUMENTS 7,901,368 B2 3/2011 Flaherty et al.
11,278,226 B2 3/2022 Heydari et al.
(Continued)

FOREIGN PATENT DOCUMENTS

WO 2015/095182 A1 6/2015

OTHER PUBLICATIONS

Xu et al. ("A 15-Channel Digital Active Electrode System for Multi-Parameter Biopotential Measurement") IEEE Transactions on Biomedical Circuits and Systems, vol. 5, No. 6, Dec. 2011 (Year: 2011).*

(Continued)

*Primary Examiner* — Christian Jang
(74) *Attorney, Agent, or Firm* — NGUYEN TARBET IP LAW

(57) ABSTRACT

This invention discloses a non-invasive electroencephalography (BEG) signal recorder and a multiband active electrode (MAE) EEG cap array. A narrow-band amplification method is disclosed that divides the desired bandwidth of the input brain signal to smaller bands, each recorded using a separate amplification path. A novel twisted differential feedback topology is disclosed for both amplifiers and active filters having ultra-high input impedance. A one-wire EEG cap array of tightly connected MAEs is disclosed that improves the flexibility and portability of the EEG cap by reducing the number of wires between the EEG cap and the host processor. Due to having MAEs embedded inside
(Continued)

electrodes, the output signals of electrodes are digital information. The tightly connected network of MAEs enables the reference electrode to be chosen dynamically. Moreover, the voltage of the reference node is adjusted using a correction feedback loop before each recording step.

6 Claims, 10 Drawing Sheets

(56) References Cited

U.S. PATENT DOCUMENTS

| | | | |
|---|---|---|---|
| 2005/0090756 | A1 | 4/2005 | Wolf et al. |
| 2006/0049957 | A1 | 3/2006 | Surgenor et al. |
| 2008/0290944 | A1 | 11/2008 | Sarpeshkar et al. |
| 2008/0294062 | A1 | 11/2008 | Rapoport et al. |
| 2008/0294579 | A1 | 11/2008 | Rapoport et al. |
| 2010/0145222 | A1 | 6/2010 | Brunnett et al. |
| 2010/0249635 | A1 | 9/2010 | Van Der Reijden |
| 2011/0282231 | A1 | 11/2011 | Pradeep et al. |
| 2012/0123289 | A1 | 5/2012 | Sorenson et al. |
| 2012/0259382 | A1 | 10/2012 | Trier et al. |
| 2012/0296444 | A1 | 11/2012 | Greenberg et al. |
| 2013/0204122 | A1 | 8/2013 | Hendler et al. |
| 2014/0180052 | A1 | 6/2014 | Lo et al. |
| 2015/0038869 | A1 | 2/2015 | Simon et al. |
| 2017/0070094 | A1 | 3/2017 | Corum et al. |
| 2017/0164863 | A1 | 6/2017 | Kennedy et al. |
| 2017/0333712 | A1 | 11/2017 | Chen |
| 2018/0303364 | A1 | 10/2018 | Yoo et al. |
| 2019/0059770 | A1 | 2/2019 | Gunasekar et al. |
| 2019/0231204 | A1 | 8/2019 | Heydari et al. |
| 2020/0121206 | A1 | 4/2020 | Dumont et al. |
| 2020/0305744 | A1 | 10/2020 | Weerakoon et al. |
| 2020/0397383 | A1 | 12/2020 | Genov et al. |
| 2020/0401226 | A1 | 12/2020 | Song et al. |
| 2022/0054830 | A1 | 2/2022 | Gooie |
| 2022/0203099 | A1 | 6/2022 | Muller et al. |
| 2022/0409903 | A1 | 12/2022 | Perryman et al. |

OTHER PUBLICATIONS

Verma et al. ("A Micro-Power EEG Acquisition SoC with Integrated Feature Extraction Processor for a Chronic Seizure Detection System") IEEE Journal of Solid-State Circuits, vol. 45, No. 4, Apr. 2010 (Year: 2010).*

Sepehrian et al. ("A Low-power Current-Reuse Dual-Band Analog Front-End for Multi-Channel Neural Signal Recording") 978-1-4244-7929-0/14/$26.00 © 2014 IEEE (Year: 2014).*

Anderson et al., "Wireless Integrated Circuit for The Acquisition of Electrocorticogram Signals", In Proceedings of 2010 IEEE International Symposium on Circuits and Systems, 2010, pp. 2952-2955.

Angeli et al., "Recovery of Over-Ground Walking after Chronic Motor Complete Spinal Cord Injury", The New England Journal of Medicine, vol. 379, No. 13, Sep. 27, 2018, pp. 1244-1250.

Ball et al., "Signal Quality of Simultaneously Recorded Invasive and Non-Invasive EEG", Neurolmage, vol. 46, 2009, pp. 708-716.

Borton et al., "An Implantable Wireless Neural Interface for Recording Cortical Circuit Dynamics in Moving Primates", Journal of Neural Engineering, vol. 10, 026010, 2013, pp. 1-16.

Brain Products GmbH, "actiCAP", Online Available at: <http://www.brainproducts.com/productdetails.php?id=4>, 2017, 2 pages.

Collinger et al., "Functional Priorities, Assistive Technology, and Brain-Computer Interfaces after Spinal Cord Injury", Journal of Rehabilitation Research & Development, vol. 50, No. 2, 2013, pp. 145-160.

Collinger et al., "High-Performance Neuroprosthelic Control by an Individual with Tetraplegia", The Lancet, vol. 381, Feb. 16, 2013, pp. 557-564.

Daliri et al., "Ultra-Low Voltage Common-Mode Voltage Detector Circuit," Electronics Letters, vol. 44, No. 13, Jun. 19, 2008, 2 pages.

Denison et al., "A 2 μW 100 nV/rtHz Chopper-Stabilized Instrumentation Am-plifier for Chronic Measurement of Neural Field Potentials", IEEE Journal of Sol-id-State Circuits, vol. 42, No. 12, Dec. 2007, pp. 2934-2945.

Do et al., "Brain-Computer Interface Controlled Robotic Gait Orthosis", Journal of NeuroEngineering and Rehabilitation, vol. 10, No. 111, 2013, pp. 1-9.

Do et al., "Sensitivity and Specificity of Upper Extremity Movements Decoded from Electrocorticogram", In 35th Annual International Conference of the IEEE Engineering in Medicine and Biology Society, Jul. 3-7, 2013, pp. 5618-5621.

Fougere et al., "Real Versus Imagined Locomotion: A [18F]-FDG PET-fMRI Comparison", Neurolmage, vol. 50, 2010, pp. 1589-1598.

Hirata et al., "A Fully Implantable Wireles! System For Human Brain-Machine Interfaces Using Brain Surface Electrodes: W-HERBS", IEICE Transactions on Communications. vol. E94B, No. 9, Sep. 2011, pp. 2448-2453.

Hochberg et al., "Neuronal Ensemble Control of Prosthetic Devices by a Human with Tetraplegia", Nature, vol. 442, Jul. 13, 2006, pp. 164-171.

Hochberg et al., "Reach and Grasp by People with Tetraplegia Using a Neu-rally Controlled Robotic Arm", Nature, vol. 485, May 17, 2012, pp. 372-375.

Hoshmand Fanavar Tehran Co., "g.SAHARAsys", g. Tec Medical Engineering Solutions, Retrieved from Internet URL: <https://hooshmandfanavar.com/en/g-tec-medical-engineering-solutions/g-saharasys/>, Accessed on: Dec. 18, 2024, 2 pages.

Javid et al., "A 4-Bit 12GS/s Data Acquisition System-On-Chip Including a Flash ADC And 4-Channel Demux in 130nm CMOS", In Proceedings of the Custom Integrated Circuits Conference, IEEE, 2012, 4 pages.

Karimi-Bidhendi et al., "CMOS Ultralow Power Brain Signal Acquisition Front ends: Design and Human Testing", IEEE Transactions on Biomedical Circuits and Systems, vol. 11, 2017, 12 pages.

Kim et al., "Thermal Impact of an Active 3-D Microelectrode Array Implanted in the Brain", IEEE Transactions on Neural Systems and Rehabilitation Engineering, vol. 15, Issue 4, Dec. 2007, pp. 493-501.

King et al., "Operation of a Brain-Computer Interface Walking Simulator for Individuals with Spinal Cord Injury", Journal of NeuroEngineering and Rehabilitation, vol. 10, No. 77, Jul. 17, 2013, 14 pages.

King et al., "The Feasibility of a Brain-Computer Interface Functional Electrical Stimulation System for The Restoration of Overground Walking After Paraplegia", Journal of NeuroEngineering and Rehabilitation, vol. 12, No. 80, 2015, pp. 1-11.

Mahajan et al. "A 64-Channel Ultra-Low Power Bioelectric Signal Acquisition System for Brain-Computer Interface", IEEE, 2015, 4 pages.

Mccrimmon et al., "Electrocorticographic Encoding of Human Gait in the Leg Primary Motor Cortex", Cerebral Cortex, Aug. 2018, pp. 2752-2762.

Muller et al., "A 0.013 mm2, 5 μW, DC-Coupled Neural Signal Acquisition IC With 0.5 V Supply," IEEE Journal of Solid-State Circuits, vol. 47, No. 1, Jan. 2012, pp. 232-243.

Neuropace, "How the RNS System Works", Retrieved from Internet URL: <http://www.neuropace.com/the-rns-system/>, retrieved on Dec. 18, 2024, 10 pages.

NEXUS-32, "Mind Media", Biofeedback and Neurofeedback Systems, 2014, 2 pages.

Repacholi et al., "Systematic Review of Wireless Phone Use and Brain Cancer and Other Head Tumors", Bioelectromagnetics, vol. 33, 2012, pp. 187-206.

Rousche et al., "Chronic Recording Capability of The Utah Intracortical Electrode Array in Cat Sensory Cortex", Journal of Neuroscience Methods, vol. 82, 1998, pp. 1-15.

Schalk et al., "Brain-Computer Interfaces Using Electrocorticographic Signals," IEEE Reviews in Biomedical Engineering, vol. 4, 2011, pp. 140-154.

(56) References Cited

OTHER PUBLICATIONS

Schmidt et al., "Biocompatibility of Silicon-Based Electrode Arrays Implanted in Feline Cortical Tissue", Journal of Biomedical Materials Research, vol. 27, No. 11, Nov. 1993, pp. 1393-1399.
Sohn et al., "Benchtop and Bedside Validation of a Low-Cost Programmable Cortical Stimulator in a Testbed For Bi-Directional Brain-Computer-Interface Research", Frontiers in Neuroscience, Jan. 12, 2023, pp. 1-19.
"Spinal Cord Injury Facts and Figures at a Glance", National Spinal Cord Injury Statistical Center (NSCIS), Feb. 2013, 2 pages.
Szmigielski, Stanislaw, "Cancer Risks Related to Low-Level RF/MW Exposures, Including Cell Phones", Electromagnetic Biology and Medicine, vol. 32, No. 3, Jan. 15, 2013, pp. 273-280.
USPTO, "Final Office Action" issued in connection with U.S. Appl. No. 16/376,831, dated Jul. 22, 2021, 22 pages.
USPTO, "Non-Final Office Action" issued in connection with U.S. Appl. No. 16/376,831, dated Jan. 6, 2021, 16 pages.
Verma et al., "A Micro-Power EEG Acquisition SoC with Integrated Feature Extraction Processor for a Chronic Seizure Detection System", IEEE Journal of Solid-State Circuits, vol. 45, No. 4, Apr. 2010, pp. 804-816.
Wang et al., "Electrocorticographic Gamma Band Power Encodes the Velocity of Upper Extremity Movements". In Proceedings of the Fifth International Brain-Computer Interface Meeting, Article 120, 2013, 2 pages.
Wang et al., "Self-Paced Brain-Computer Interface Control of Ambulation in a Virtual Reality Environment", Journal of Neural Engineering, vol. 9, 056016, 2012, pp. 1-12.
Wang et al., "State and Trajectory Decoding of Upper Extremity Movements from Electrocorticogram", In Proceedings of 6th International IEEE/EMBS Conference on Neural Engineering, Nov. 6-8, 2013, pp. 969-972.
Wattanapanitch et al., "An Energy-Efficient Micropower Neural Recording Amplifier", IEEE Transactions on Biomedical Circuits and Systems, vol. 1, No. 2, Jun. 2007, pp. 136-147.
WIPO, "International Preliminary Report on Patentability" issued in connection with PCT Patent Application PCT/US2017/055652, dated Apr. 18, 2019, 6 pages.
WIPO, "International Preliminary Report on Patentability" issued in connection with PCT Patent Application PCT/US2021/062602, dated Jun. 22, 2023, 7 pages.
WIPO, "International Search Report and Written Opinion" issued in connection with PCT Patent Application PCT/US2023/068700, dated Jan. 10, 2024, 13 pages.
WIPO, "International Search Report and Written Opinion" issued in connection with PCT Patent Application PCT/US2017/055652, dated Dec. 22, 2017, 7 pages.
WIPO, "International Search Report and Written Opinion" issued in connection with PCT Patent Application PCT/US2021/062602, dated Apr. 1, 2022, 10 pages.
WIPO, "International Search Report and Written Opinion" issued in connection with PCT Patent Application PCT/US23/81377, dated Apr. 18, 2024, 13 pages.
Wang, B. H. Calhoun, and A. P. Chandrakasan, Sub-threshold Design for Ultra Low-Power Systems, Springer, 2006, vol. 95.
Razavi B. Design of integrated circuits for optical communications. John Wiley & Sons, 2012.

* cited by examiner

HIGH RESOLUTION ELECTROENCEPHALOGRAPH SIGNAL ACQUISITION SYSTEM

CROSS-REFERENCES TO RELATED APPLICATIONS

This application claims benefit of U.S. Provisional Application No. 63/123,160 filed Dec. 9, 2020, the specification of which is incorporated herein in its entirety by reference.

BACKGROUND OF THE INVENTION

Field of the Invention

The present invention relates to medical sensing of human subjects, in particular to non-invasive electroencephalograph acquisition.

Background Art

The Electroencephalography (EEG) signal recording is a totally non-invasive brain signal acquisition technique from the scalp capable of being used in Brain-Computer Interfaces (BCI) to promote motor recovery in individuals who suffer from stroke or Spinal Cord Injury (SCI). It also plays a considerable role in the treatment of epilepsy and monitoring anesthesia in the operating room. The EEG recording method similar to its invasive counterpart, Electrocorticography (ECoG) signal acquisition, bypasses the injured spinal cord and directly connects the brain to artificial exoskeletons. Even though some fundamental movement abilities could be recovered using EEG signal recorders, however, their application is limited due to the need to use cumbersome cables and connectors (between the EEG cap and the recorder device), suffering from noisy environment, having low input bandwidth, and inadequate spatial resolution. EEG signals are divided into different frequency bands, δ (0.5 Hz-3 Hz), θ (4 Hz-7 Hz), α (8 Hz-13 Hz), β (14 Hz-30 Hz), γ (31 Hz-59 Hz), high-γ (60 Hz-200 Hz). During sleep, EEG signals mostly contain large-amplitude low-frequency oscillations, yet they mainly include small-amplitude high-frequency components when we are awake and paying attention to something. Recently, high-frequency brain signals such as γ and high-γ bands have become more attractive due to their relation to the working memory and attention. It has been shown that for some diseases like Alzheimer, Parkinson, Schizophrenia, and Epilepsy, γ-band brain signals demonstrate abnormal activity. Some studies postulate that high-γ brain signals are exactly similar to γ-band signals but at higher frequencies, while some others believe that high-γ band signals are related to spiking activity in the brain. In particular, some research claims a strong correlation between high-γ band brain signals and spiking activity in the brain suggesting that high-γ band activity is a trustworthy electrophysiological indication of neuronal firing near electrodes. The performance of recording brain signals using EEG procedures suffers from having low-amplitude waveforms and an extremely noisy environment full of physiological (such as muscular artifacts, cardiac rhythm, and eye movement) and technical artifacts (such as movement or disconnection in wires). Moreover, studies show that the higher the frequency of brain signals, the lower the amplitude of them. Therefore, detecting high-frequency bands of EEG signals (higher than 30 Hz) is quite challenging due to the fact that the commercial EEG recorders suffer from low input bandwidth. Portability is another important feature that cannot be easily achieved because of using huge wire connectors and numerous wired interconnections. It goes without saying that the aforementioned issues become even bolder when high spatial resolution (large number of electrodes) is required. In addition, most of the previously reported EEG signal recorders are designed to use wet electrodes that exert conductive gel to lower the impedance of the electrode-tissue interface. Using wet electrodes mandates gel application and skin cleaning that must be done by a trained technician in a medical clinic. They also prone to lose their quality after several hours requiring another round of gel application that is neither comfortable for the patient nor desirable for the technician. To replace them with their dry equivalence (that have larger electrode-tissue interface impedance) and ease the process of EEG signal recording even for home-setting applications, it is compulsory to design ultra-high input impedance amplification stages to eliminate the possible voltage division causing amplitude reduction in the recorded signal. It is worth noting that the large electrode-tissue impedance and as a result the resistive voltage division between the electrode and the input of the amplification chain cause a drastic systematic mismatch for the recording systems that use a shared reference. This mismatch results in considerable degradation of the Common-Mode Rejection Ratio (CMRR) of the chain, thereby making it susceptible to common-mode environmental noises (such as power-line noises).

Although many prior works proposed various methods to record EEG signals, none of them suggested a promising technique to deal with unpredictable artifacts and background noises that can easily corrupt the desired signal. When it comes to low-amplitude high-frequency brain signals, the sensitivity of the amplifier becomes very important. On one hand, recording low-amplitude signals requires a very high voltage gain amplifier chain. On the other hand, low-voltage circuit design and consequently limited headroom voltage is necessary for lowering the power consumption of the system. Therefore, the immunity to saturation induced by large artifacts and simultaneously having a high sensitivity to capture the desired signal are the two most significant requirements for any EEG recorder that targets wide-band brain signals. As mentioned before, in order to use dry electrodes, the input impedance of the recording system must be extremely high ensuring high-quality signal acquisition. For instance, a positive feedback loop is used in some EEG acquisition system to increase the input impedance. This technique makes the circuit potentially unstable owing to the unstable nature of positive feedback loops. Another technique called feed-forward auxiliary path is presented. This technique gives rise to the power consumption of the circuit and increases the random mismatches at the input stage especially in case of having an array of signal recorders. To further exemplify, power-hungry buffers are used to bolster the input impedance. These single-input single-output amplifiers are the main source of random mismatches and hence reduce the CMRR of the circuit. Lastly and most importantly, portability, flexibility, and having high spatial resolution (more electrodes) at the same time is obligatory for EEG signal recorders. In fact, traditional EEG signal recording systems are extremely colossal making them useless for chronic EEG monitoring or wearable devices. These systems use multiple wires and connectors to interface the EEG cap and the recording device that results in inelasticity and immovability.

All the aforementioned drawbacks and shortcomings encouraged us to discover the presented innovation where a novel EEG recording system including a one-wire tightly-connected network of Built-in-Electrode Chips EEG cap (makes the system flexible and portable) is disclosed that uses narrow-band amplifiers to magnify the sensitivity of the system and a unique twisted differential feedback topology to increase the input impedance (can be used for designing of both amplifiers and active filters). The proposed invention is capable of recording high-frequency brain signals and extracting all the required information while remaining totally non-invasive; thereby, it is able to be used as an equivalent of invasive methods such as ECOG signal recording techniques. As a result of embedding small chips in electrodes and making a tightly connected network of processors, it is possible to define a dynamic referencing method that contributes to improving the CMRR of the circuit, preventing the circuit from saturation due to offset voltages and common-mode noises, and removing artifacts. Multiple other methods are also used to impede the amplifier chain from saturation and remove signal contaminations. Parallel acquisition and computation of brain signal from all the available electrodes on the EEG cap is another advantage of the proposed built-in-electrode chip EEG cap that makes the real-time signal recording practical. Additional traits and attributes of the revealed invention are evident in the subsequent comprehensive explanations and claims.

BRIEF SUMMARY OF THE INVENTION

It is an objective of the present invention to provide systems that allow for non-invasive acquisition of electroencephalograph (EEG) signals, as specified in the independent claims. Embodiments of the invention are given in the dependent claims. Embodiments of the present invention can be freely combined with each other if they are not mutually exclusive.

The presented invention includes an EEG signal acquisition system and a unique EEG cap that is designed to capture wide-band brain signals including δ, θ, α, β, γ and high-γ bands with a completely non-invasive approach. High sensitivity, immunity to saturation in the existence of large artifacts, high input impedance, having a tightly connected network of multiband active electrodes (MAEs), and simplicity in the cap-recorder interface are some of the features covered by the proposed innovation. A narrow-band amplification technique is employed to bolster the sensitivity of the amplifier chain by lowering the integrated input-referred noise per each path. This technique filters the input signal using multiple high input-impedance active narrow-band band-pass filters (BPF) that not only satisfy the requirement of having high input impedance but also have an in-band gain (larger than one) to capture low-amplitude input signals. For EEG signal acquisition, the most desirable method is to use dry electrodes due to the ease of using them out of clinics or hospitals. However, dry electrodes demonstrate a higher impedance compared to the wet ones resulting in amplitude degradation when the input impedance of the amplifier is not high enough. To achieve high input impedance and eliminate this issue, the twisted differential feedback topology (for both amplifiers and active filters) is designed that isolates the input port from the feedback loop by using two auxiliary feedback paths.

Since the presented invention targets high-frequency brain signals which have low amplitudes, a high voltage gain is required to amplify the signal raising the probability of saturation in the chain. Moreover, large artifacts (both patient related or technical) are the main source for signal contamination and amplifier saturation. Dealing with artifacts, multiple techniques are used to lessen the effects of them and make the amplification chain more robust. Firstly, right after filtering the signal using a narrow-band BPF, the voltage signal is converted to current using a voltage to current converter (VIC) because the voltage headroom limitation does not exist in the current domain. Then, the current-domain artifact cancellation block that is controlled by some digital signals generated by the digital processor detects artifacts and removes them. After removing artifacts in the current domain and retaining the desired signal, it is safe to revert back to the voltage domain and finally, digitize the amplified signal. Secondly, the programmable gain amplifier (PGA) controlled by the digital data and an active local feedback loop (saturation prevention loop) modifies the gain of the chain to impede it from saturation.

Above all, a novel one-wire EEG cap is presented that includes a network of electrodes closely linked to each other. Inside each electrode, a tiny chip is embedded that has two major analog and digital parts. The analog part consists the pre-described analog datapath, and the digital part provides the analog part with suitable control signals (such as signals used for artifact cancellation), stores the quantized data, and shifts the digital data to other electrodes. Since each MAE has a digital processor, and therefore the output signal of each MAE is a digital data (as opposed to traditional EEG caps where the output signal of each electrode is analog), it is feasible to multiplex all the digital bits and serialize them. Thus, the whole EEG cap uses only one wire that carries a serial digital signal. This approach makes the EEG cap extremely flexible and reduces the technical artifacts created by moving wires. Also, since each electrode has its own chip, it can record the brain signal independently. Therefore, the information of all electrodes can be acquired in real-time.

In the new EEG cap array, all embedded chips are connected together through local wires and data shifters. Therefore, they can communicate and share information among each other to better catch the desired signal and detect contaminations. Each electrode is able to work as a read-out node or as a reference point. It means the reference electrode can be chosen dynamically that helps decrease the systematic mismatches caused by having a fixed shared reference electrode. Indeed, a shared reference sees a different impedance from all the amplifiers it is connected to compared to other electrodes that each of them sees only one amplifier. One way to avoid this systematic imbalance is to use the new technique of having a dynamic reference. Another advantage of the presented EEG cap is the use of average referencing method that is useful to remove common-mode noises and random mismatches. Assuming that all components can be fabricated ideally without any mismatch, the small-signal voltage value of the reference electrode must be zero. However, in the real world, the voltage value of the reference should be a non-zero value compensating for the common-mode noises and mismatch-related offset voltages. Thanks to having a tightly linked network of MAEs, it is feasible to use a correction feedback loop that monitors the voltage of all electrodes, finds the average of them, and finally calculates the most optimum voltage value for the reference electrode accordingly. This process is done before each brain-signal recording step to guarantee that the reference voltage has the best value preventing the amplifier chain from saturation and also the recorded signal from contamination.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

The features and advantages of the present invention will become apparent from a consideration of the following detailed description presented in connection with the accompanying drawings in which.

DETAILED DESCRIPTION OF THE INVENTION

Following is a list of elements corresponding to a particular element referred to herein:

1000 system of smart sensors
1100 plurality of sensor electrodes
1110 sensor electrode
1111 multiband active electrode (MAE)
1200 digital nearest-neighbor network (DNNN)
1300 one-wire network (1WN)
1400 1WN branch selector (1WNBS)
1410 inner interface
1420 outer interface
1500 global clock (CLK)
1600 flexible locating surface
1700 host access port
2000 system for digitizing electroencephalograph (EEG) electrode signals (SYSCHIP)
2100 analog datapath (ADPATH)
2110 electrical potential sensing port (AlN)
2120 wide-band acquisition block (WB)
2121 analog-to-digital converter (ADC)
2122 amplifier (AMP)
2123 preamplifier-filter (PREFILT)
2130 narrow-band acquisition block (NB)
2131 analog-to-digital converter (ADC)
2132 tuned channel (TUNER)
2133 amplifier (AMP)
2134 low-pass filter (LPF)
2135 mixer (MIXER)
2136 artifact cancellation block (CANCEL)
2137 preamplifier-filter (PREFILT)
2150 collating serializer (MUX)
2200 digital processor (CPU)
2210 control input port (CTRLI)
2215 control output port (CTRLO)
2221 first digital nearest-neighbor network port (DNNNP1)
2222 second digital nearest-neighbor network port (DNNNP2)
2223 third digital nearest-neighbor network port (DNNNP3)
2224 fourth digital nearest neighbor network port (DNNN4)
2231 first one-wire network port (1WNP1)
2232 second one-wire network port (1WNP2)
2240 application-specific digital hardware (ASDH)
2300 digital clock input (CLK)
3100 first transconductor
3110 first transconductor non-inverting input terminal (VIN1P)
3120 first transconductor inverting input terminal (VIN1N)
3130 first transconductor non-inverting output terminal (IOUT1P)

3140 first transconductor inverting output terminal (IOUT1N)

3200 second transconductor

3210 second transconductor non-inverting input terminal (VIN2P)

3220 second transconductor inverting input terminal (VIN2N)

3230 second transconductor non-inverting output terminal (IOUT2P)

3240 second transconductor inverting output terminal (IOUT2N)

3300 first feedback impedance

3310 first feedback impedance positive terminal (ZF1P)

3320 first feedback impedance negative terminal (ZF1N)

3400 second feedback impedance

3410 second feedback impedance positive terminal (ZF2P)

3420 second feedback impedance negative terminal (ZF2N)

3500 spanning impedance

3510 positive terminal (ZXP)

3520 negative terminal (ZXN)

Figure 1:
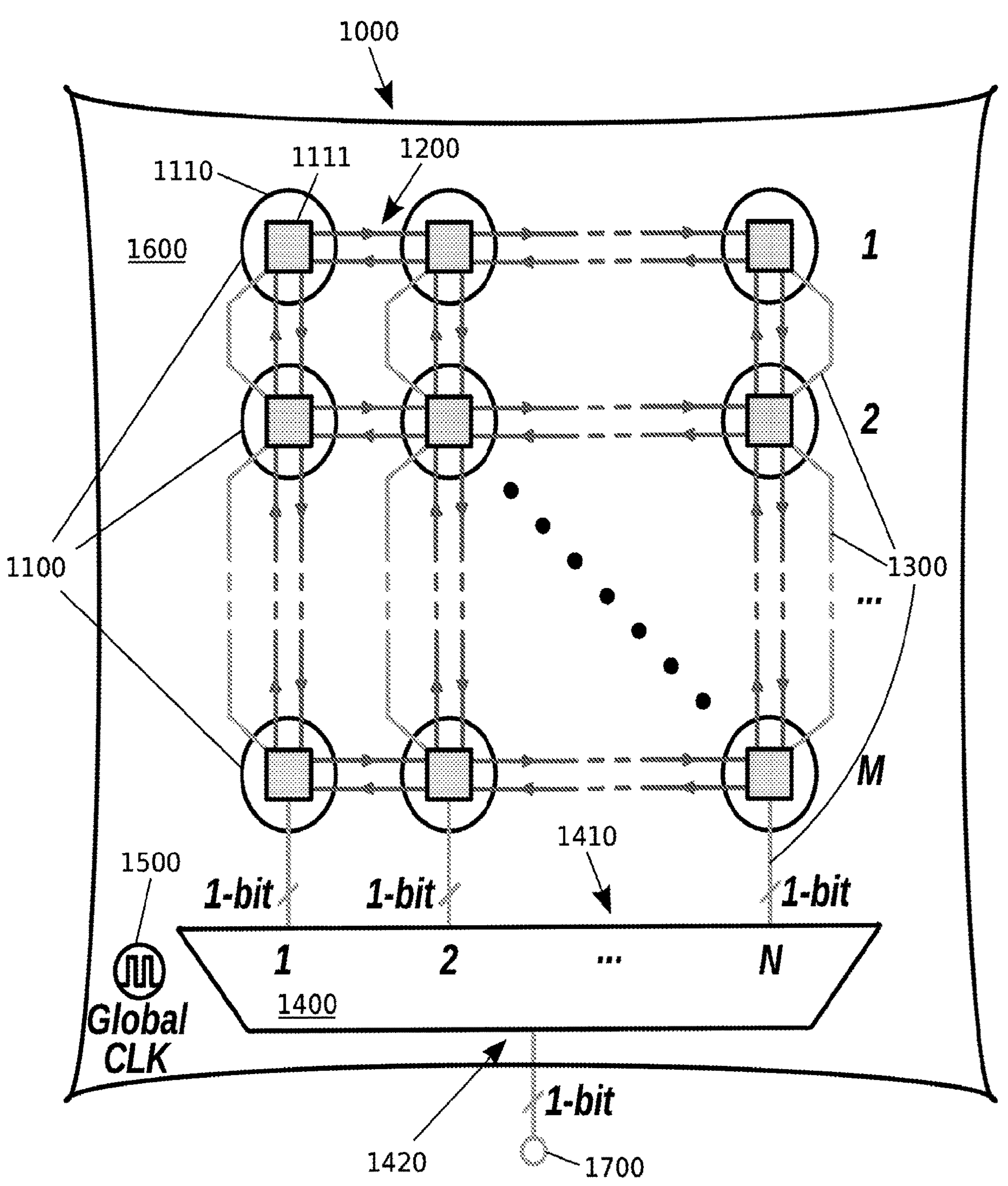
FIG. 1 shows a block diagram of a system of smart sensors (1000) for electroencephalograph (EEG) acquisition, also referred to as an EEG cap. The EEG cap may be worn on the scalp of a medical subject. The system of smart sensors (1000) comprises a two-dimensional (2D) array of sensor electrodes (1110), each of which comprises a multiband active electrode (MAE) (1111). The 2D array of sensor electrodes (1110) resides on a flexible locating surface (1600), and thereby constitutes the EEG cap. Sensor data from the EEG cap is delivered to the host access port (1700), for analysis by a host processor.

Referring now to FIG. 1, the present invention features a system of smart sensors (1000) for electroencephalograph (EEG) acquisition. The system of smart sensors (1000) may comprise N pluralities of sensor electrodes (1100), wherein each plurality of sensor electrodes (1100) may comprise M sensor electrodes (1110), wherein each sensor electrode (1110) may comprise a multiband active electrode (MAE) (1111), wherein N may be a fixed positive integer, and wherein M may be a fixed positive integer.

The system of smart sensors (1000) may comprise a plurality of digital nearest-neighbor networks (DNNN) (1200), and a plurality of one-wire networks (1WN) (1300), N in number. The system of smart sensors (1000) may comprise a 1WN branch selector (1WNBS) (1400), which may comprise an inner interface (1410) and an outer interface (1420), a global clock (1500), and a host access port (1700). The system of smart sensors (1000) may comprise a flexible locating surface (1600).

Each sensor electrode (1110) may be mounted to the flexible locating surface (1600), and the location and orientation of each sensor electrode (1110) with respect to the flexible locating surface (1600) may be fixed, and the orientation of every sensor electrode (1110) with respect to the flexible locating surface (1600) may be about identical. The position of each sensor electrode (1110) may be indexed by a respective pair of integer Cartesian coordinates, and each respective pair of integer Cartesian coordinates may be unique in the space (m, n), and m may lie in the range of 1 to M, inclusive, and n may lie in the range of 1 to N, inclusive. In some embodiments each sensor electrode (1110) may neighbor at most 4 adjacent sensor electrodes (1110).

Each MAE (1111) may be mounted to its respective sensor electrode (1110), and the orientation of all MAEs (1111) with respect to their respective sensor electrodes (1110) may be about identical. Each DNNN (1200) may lie interstitial to its two adjacent MAEs (1111), and a given DNNN (1200) may connect electrically the two MAEs (1111) adjacent to the given DNNN (1200), and the plurality of DNNNs (1200) may be $2 \cdot M \cdot N - M - N$ in number. Each 1WN (1300) may connect electrically all M of the MAEs (1111) that may belong to the parent plurality of sensor electrodes (1100). The inner interface (1410) of the 1WNBS (1400) may connect electrically, individually, to each 1WN (1300), and the outer interface (1420) of the 1WNBS (1400) may connect to a host access port (1700).

The CLK (1500) may connect electrically to each MAE (1111), and the CLK (1500) may connect electrically to the 1WNBS (1400). Each sensor electrode (1110) may sense an electric potential at the location of the respective sensor electrode (1110), and each sensor electrode (1110) may connect electrically to its respective MAE (1111). Each MAE (1111) may digitize the electric potential within several frequency bands at its respective location, with respect to some common reference electric potential, and the system of smart sensors (1000) may employ a distributed algorithm that may cause the common reference electric potential to be variously assigned so as to reduce the shared-reference induced mismatches. The plurality of 1 WNs (1300) and the 1WNBS (1400) may deliver the digitized electrode potentials to the host access port (1700), and the MAEs (1111) may network with each other via the plurality of DNNNs (1200) in a self-organizing fashion, so as to digitize and serialize sensor electrode (1110) potentials.

Figure 2:
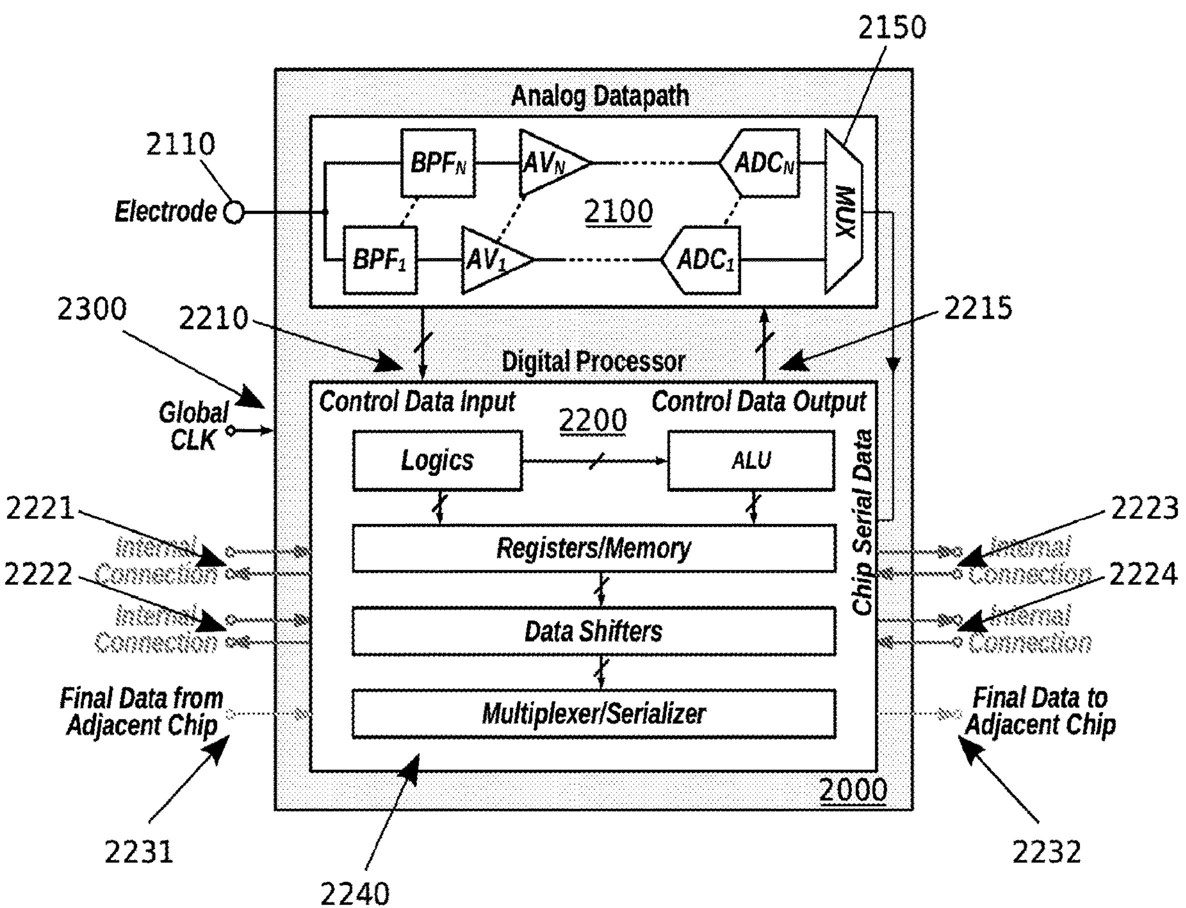
FIG. 2 shows a block diagram of a system for digitizing electroencephalograph (EEG) electrode signals (SYSCHIP) (2000), also referred to as a multiband active electrode (MAE) (1111). The SYSCHIP (2000) comprises an analog datapath (ADPATH) (2100), an electrical potential sensing port (AlN) (2110), and a digital processor (CPU) (2200).
Figure 3:
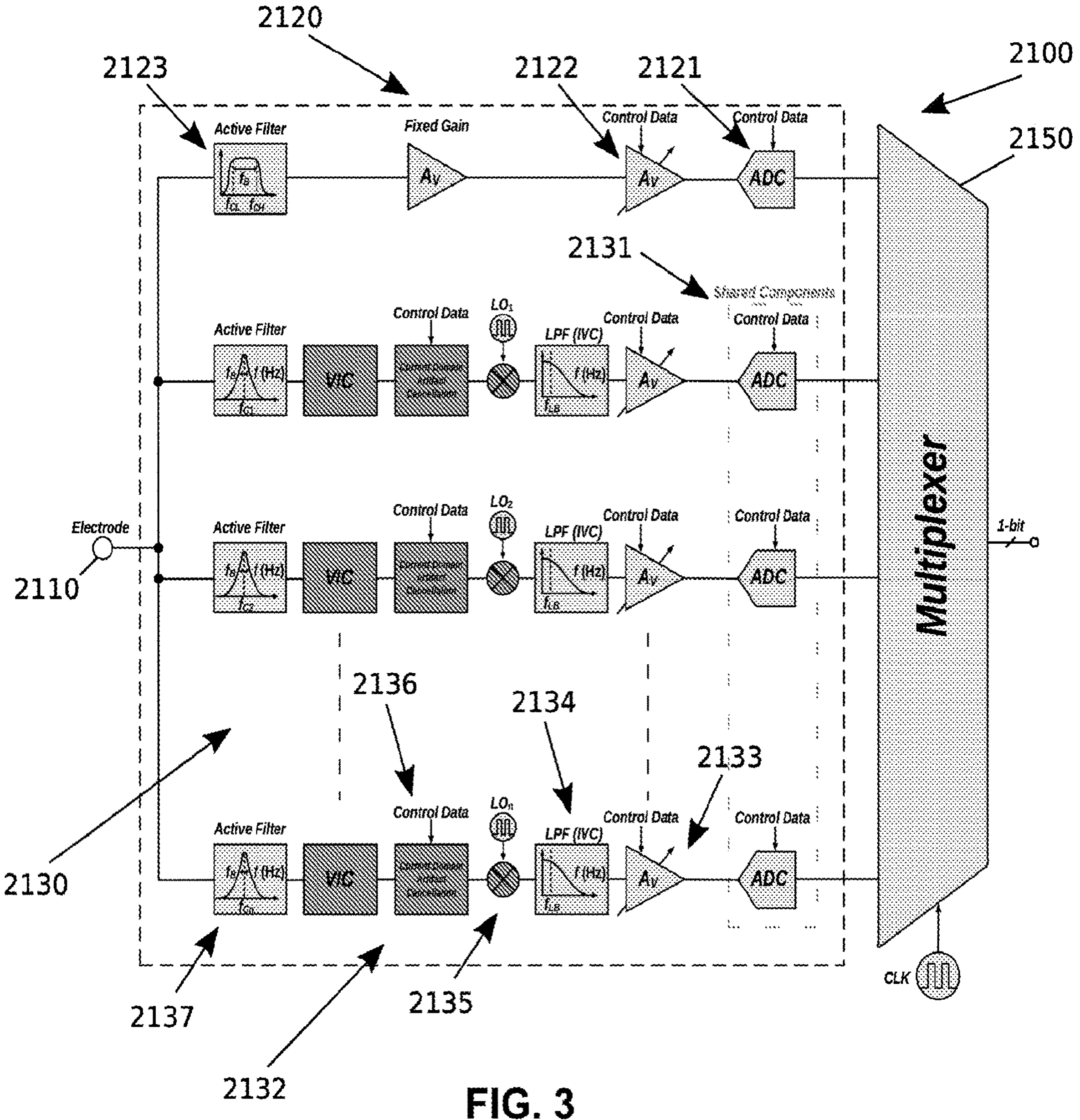
FIG. 3 shows a detailed block diagram of the ADPATH (2100) section of the SYSCHIP (2000). The ADPATH (2100) comprises a wide-band acquisition block (WB) (2120) and a narrow-band acquisition block (NB) (2130), both of which process signals arriving from the AlN (2110). The WB (2120) and the NB (2130) send their digitized data to the collating serializer (MUX) (2150).

Referring now to FIGS. 2 and 3, the present invention features a system for digitizing electroencephalograph (EEG) electrode signals (SYSCHIP) (2000). The SYSCHIP (2000) may comprise an analog datapath (ADPATH) (2100), a digital processor (CPU) (2200), and a digital clock input port (CLK) (2300). The analog datapath (ADPATH) (2100) may comprise an electrical potential sensing port (AlN) (2110), a wide-band acquisition block (WB) (2120), a narrow-band acquisition block (NB) (2130), and a collating serializer (MUX) (2150). The wide-band acquisition block (WB) (2120) may comprise an analog-to-digital converter (ADC) (2121), an amplifier (AMP) (2122), and a preamplifier-filter (PREFILT) (2123). The narrow-band acquisition block (NB) (2130) may comprise an analog-to-digital converter (ADC) (2131), and a plurality of tuned channels (TUNER) (2132). Each TUNER (2132) may comprise an amplifier (AMP) (2133), a low-pass filter (LPF) (2134), a mixer (MIXER) (2135), an artifact cancellation block (CANCEL) (2136), and a preamplifier-filter (PREFILT) (2137).

A digital processor (CPU) (2200) may comprise a control input port (CTRLI) (2210), a control output port (CTRLO) (2215), a first digital nearest-neighbor network port (DNNNP1) (2221), a second digital nearest-neighbor network port (DNNNP2) (2222), a third digital nearest-neighbor network port (DNNNP3) (2223), a fourth digital nearest-neighbor network port (DNNNP4) (2224), a first one-wire network port (1WNP1) (2231), a second one-wire network port (1WNP2) (2232), and an application-specific digital hardware (ASDH) (2240). The ADPATH (2100) and the CPU (2200) together may constitute an integrated circuit. The ADPATH MUX (2150) may connect electrically to the CPU (2200), and the CPU CTRLI (2210) may connect electrically to the ADPATH (2100), and the CPU CTRLO (2215) may connect electrically to the ADPATH (2100). The CLK (2300) may connect electrically to the CPU (2200), and the CLK (2300) may connect electrically to the ADPATH (2100).

The AlN (2110) may connect electrically to the WB PREFILT (2123), and the WB PREFILT (2123) may connect electrically to the WB AMP (2122), and the WB AMP (2122) may connect electrically to the WB ADC (2121), and the WB ADC (2121) may connect electrically to the ADPATH MUX (2150). The AlN (2110) may connect electrically to each of the NB PREFILTs (2137) belonging to the plurality of TUNERs (2132). Each NB PREFILT (2137) may connect electrically to its respective NB CANCEL (2136), and each NB CANCEL (2136) may connect electrically to its respective NB MIXER (2135), and each NB MIXER (2135) may connect electrically to its respective NB LPF (2134). Each NB LPF (2134) may connect electrically to its respective NB AMP (2133), and each NB AMP (2133) may connect electrically to the NB ADC (2131). The NB ADC (2131) may connect electrically to the ADPATH MUX (2150).

The DNNNP1 (2221) may connect electrically to the ASDH (2240), and the DNNNP2 (2222) may connect electrically to the ASDH (2240), and the DNNNP3 (2223) may connect electrically to the ASDH (2240), and the DNNNP4 (2224) may connect electrically to the ASDH (2240). The CTRLI (2210) may connect electrically to the ASDH (2240), and the CTRLO (2215) may connect electrically to the ASDH (2240). The 1WNP1 (2231) may connect electrically to the ASDH (2240), and the 1WNP2 (2232) may connect electrically to the ASDH (2240). The 1WNP1 (2231) may receive and may forward digitized EEG signals from an adjacent SYSCHIP (2000) to the 1WNP2 (2232) via the CPU (2200), and the CPU (2200) may deliver digitized EEG signals from the ADPATH (2100) to the 1WNP2 (2232).

The CPU (2200) may communicate and may negotiate control and configuration information with at most four adjacent SYSCHIPs (2000) via the DNNNP1 (2221), the DNNNP2 (2222), the DNNNP3 (2223), and the DNNNP4 (2224), respectively. The WB PREFILT (2123) may present an input impedance to the AlN (2110) about commensurate with that of a metal-oxide-semiconductor field-effect transistor (MOSFET) gate, and each NB PREFILT (2137) may present an input impedance to the AlN (2110) about commensurate with that of a MOSFET gate. The WB PREFILT (2123) may perform a bandpass filtering and amplification operation upon the electrical signal present at the AlN (2110).

The voltage gain of the WB AMP (2122) and voltage gain of the WB ADC (2121) may be coordinated by the CPU to modulate the range of signals faithfully digitized while maintaining constant weighting of the WB ADC (2121) least-significant bits. Each of the NB PREFILTs (2137) may perform a narrow-band bandpass filtering and amplification operation upon the electrical signal present the AlN (2110). The passbands of each of the NB PREFILTs (2137) may be separate from each other, and separate from the passband of the WB PREFILT (2123). The voltage gain of each NB AMP (2133) and the voltage gain of its respective NB ADC (2131) may be coordinated by the CPU (2200) to modulate the range of signals faithfully digitized while maintaining constant weighting of the NB ADC (2131) least-significant bits. Each NB CANCEL (2136) may remove signal artifacts in the current domain, and each NB MIXER (2135) and its respective NB LPF (2134) may downconvert its respective passband to about a minimum-bandwidth signal representation.

The NB ADC (2131) may employ a separate sample-and-hold circuit for each TUNER (2132). The ADPATH MUX (2150) may collate bitstream data from the WB ADC (2121) and the NB ADC (2131) for delivery to the CPU (2200). The data stream delivered by the ADPATH (2100) may constitute about an optimal filter for maximizing the signal-to-noise ratio (SNR) with respect to EEG signal statistics, so as to faithfully record EEG signals.

Figure 4:
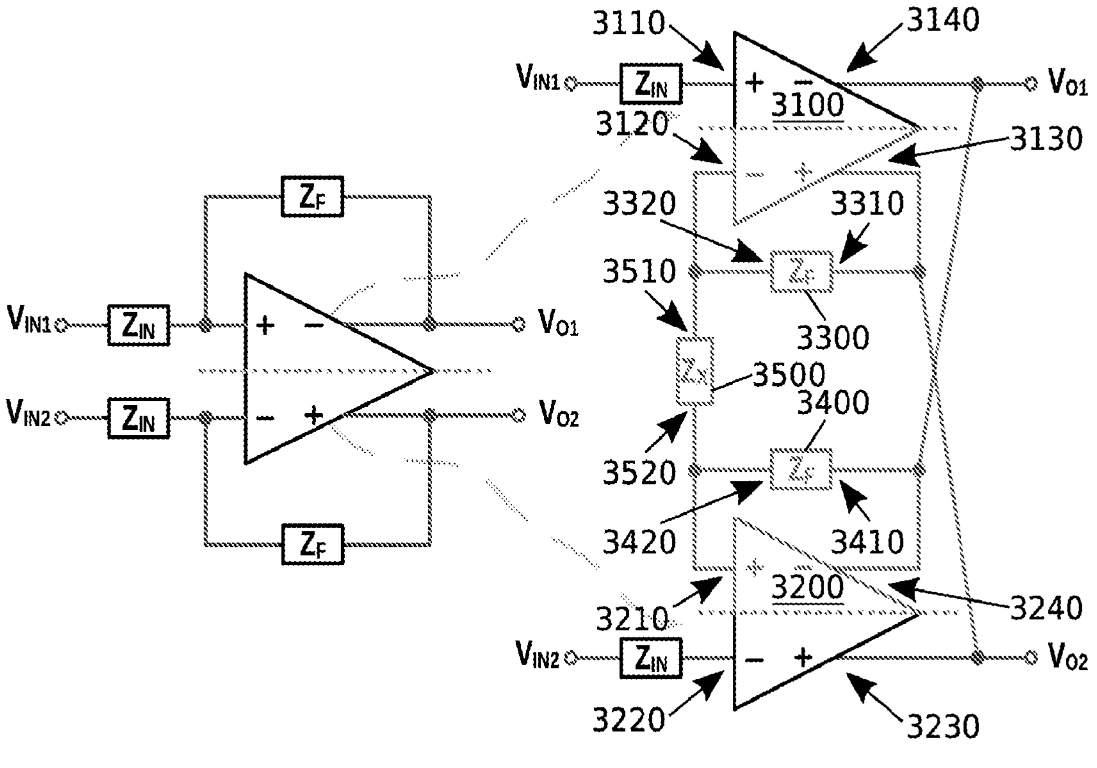
FIG. 4 shows a block diagram of a structure for differential amplification and active filtering, also referred to as a twisted differential feedback topology. The block diagram comprises a first transconductor (3100), a second transconductor (3200), a first feedback impedance (3300), a second feedback impedance (3400), and a spanning impedance (3500), along with their associated electrical interconnect.

Referring now to FIG. 4, the present invention features a structure for differential amplification and active filtering. The structure for differential amplification and active filtering may comprise a first transconductor (3100), having transconductance GM1. The first transconductor (3100) may comprise a non-inverting input terminal (VIN1P) (3110), an inverting input terminal (VIN1N) (3120), a non-inverting output terminal (IOUT1P) (3130), and an inverting output terminal (IOUT1N) (3140). The structure for differential amplification and active filtering may comprise a second transconductor (3200), having transconductance GM2. The second transconductor may comprise a non-inverting input terminal (VIN2P) (3210), an inverting input terminal (VIN2N) (3220), a non-inverting output terminal (IOUT2P) (3230), and an inverting output terminal (IOUT2N) (3240).

The structure for differential amplification and active filtering may comprise a first feedback impedance (3300), having value ZF1, and the first feedback impedance (3300) may comprise a positive terminal (ZF1P) (3310), and a negative terminal (ZF1N) (3320). The structure for differential amplification and active filtering may comprise a second feedback impedance (3400), having value ZF2, and the second feedback impedance (3400) may comprise a positive terminal (ZF2P) (3410), and a negative terminal (ZF2N) (3420). The structure for differential amplification and active filtering may comprise a spanning impedance (3500), having impedance ZX, and the spanning impedance (3500) may comprise a positive terminal (ZXP) (3510), and a negative terminal (ZXN) (3520).

The IOUT1N (3140) may connect electrically to the IOUT2N (3240); wherein the IOUT1P (3130) may connect electrically to the IOUT2P (3230). The ZF1P (3310) may connect electrically to the IOUT1P (3130), and the ZF1N (3320) may connect electrically to the VIN1N (3120). The ZF2P (3410) may connect electrically to the IOUT2N (3240); wherein the ZF2N (3420) may connect electrically to the VIN2P (3210). The ZXP (3510) may connect electrically to the VIN1N (3120), and the ZXN (3520) may connect electrically to the VIN2P (3210). The current transported within the first transconductor (3100) from the IOUT1N (3140) to the IOUT1P (3130) may equal GM1*(V(VIN1P)-V(VIN1N)), wherein V(VIN1P) designates the voltage on the VIN1P (3110), and wherein V(VIN1N) designates the voltage on the VIN1N (3120). The current transported within the second transconductor (3200) from the IOUT2N (3240) to the IOUT2P (3230) may equal to GM2*(V(VIN2P)-V(VIN2N)), wherein V(VIN2P) designates the voltage on the VIN2P (3210), and wherein V(VIN2N) designates the voltage on the VIN2N (3220), and wherein GM1 may be about equal to GM2.

The structure for differential amplification and active filtering may isolate the first feedback impedance (3300), the second feedback impedance (3400), and the spanning impedance (3500) from the VIN1P (3110). The structure for differential amplification and active filtering may isolate the first feedback impedance (3300), the second feedback impedance (3400), and the spanning impedance (3500) from the VIN2N (3220). The structure for differential amplification and active filtering may make the differential-mode gain about equal to (ZF1+ZX+ZF2)/ZX.

In some embodiments, MOSFETs may constitute the first transconductor (3100) and the second transconductor (3200), and some of the plurality of MOSFETs may participate in the formation of both the first transconductor (3100) and the second transconductor (3200), where the merging of their circuit paths may permit. In some embodiments, the differential-mode gain expression may be modified to alpha*(ZF1+ZX+ZF2)/ZX, where alpha may designate the ratio of the transconductance of the input MOSFETs to that of the auxiliary MOSFETs.

Example

The following is a non-limiting example of the present invention. It is to be understood that said example is not intended to limit the present invention in any way. Equivalents or substitutes are within the scope of the present invention.

Motivation and Objective

Electroencephalography (EEG) is a ubiquitous non-invasive neuroimaging modality with numerous clinical, scientific, and technological applications. EEG is commonly used for the diagnosis of conditions such as epilepsy, sleep disorders, and alterations of consciousness. Unlike alternative neuroimaging techniques, such as functional magnetic resonance imaging (fMRI) or magnetoencephalography (MEG), EEG requires relatively simple recording equipment which, in turn, places very few constraints on the design and execution of scientific experiments. Therefore, EEG has been the neuroimaging method of choice in many science disciplines such as neuroscience, cognitive science, and psychophysics. This modality has been increasingly used in the emerging field of brain-computer interfaces (BCIs) with the potential of restoring motor function to people with paralysis. Recently, its use has been expanded to consumer/wearable electronics, primarily as a source of bio-feedback or a control signal for computer gaming applications. Other non-clinical uses of EEG include mental workload monitoring and enhancement of cognitive function. EEG has also been used in neuro-feedback practice with a potential for both clinical and nonclinical applications.

Figure 5:
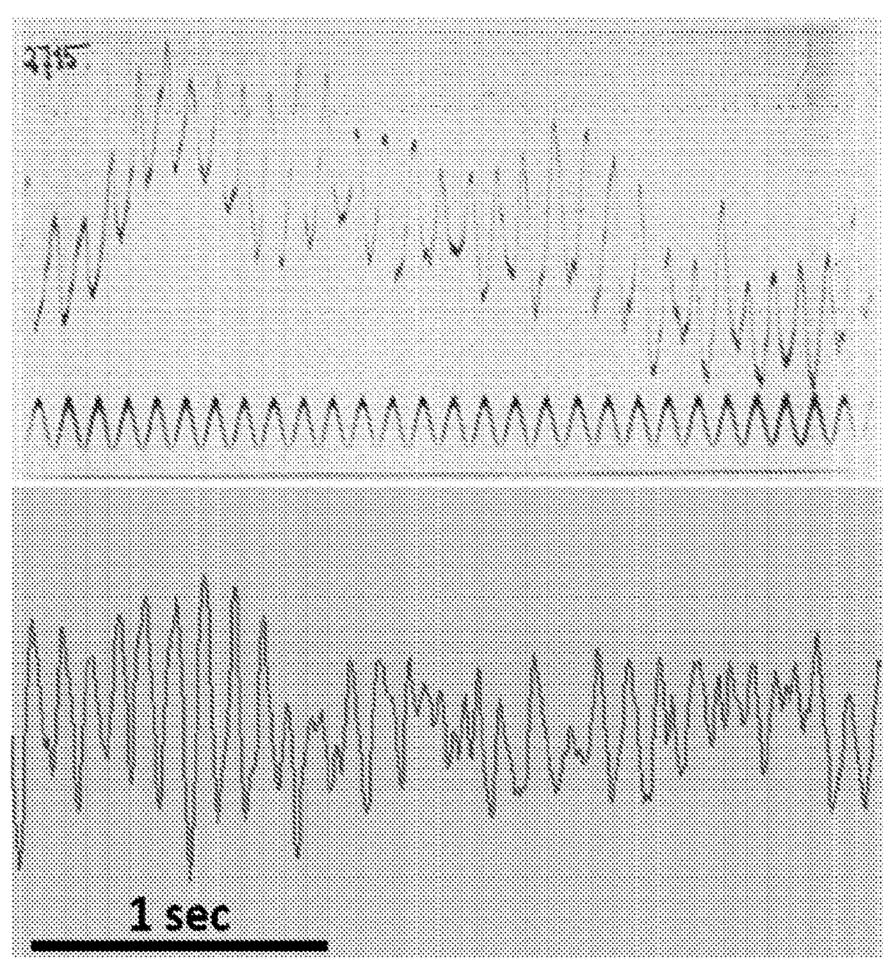
FIG. 5 shows (Top) an EEG α-wave (8-12 Hz) in reference to a 10-Hz sine wave recorded by Berger in 1929 using a double-coil galvanometer. (Bottom) A duration-matched EEG α-wave recorded using a modern state-of-the-art EEG system.

Despite its widespread use and numerous technological advancements, the quality of EEG signals recorded by scalp electrodes has not substantially improved in nearly 100 years. To underscore this point, FIG. 5 juxtaposes an early EEG recording by Hans Berger (the inventor of EEG) and a modern-day EEG signal recorded by our group. The spatial and temporal resolutions in contemporary EEG remain limited due to the fundamental properties of the human skull and underlying head tissues, which act as a low-bandwidth spatio-temporal filter. Consequently, useful EEG signals captured by commercial recording systems are typically confined to the 0-30 Hz frequency range. However, brain field potentials strongly correlate with cognitive and behavioral processes in frequency bands above 30 Hz, which remains beyond the reach of conventional EEG recording systems. Likewise, the spatial resolution of conventional EEG is few centimeters, which far exceeds the size of cortical columns or even the entire cortical areas that are responsible for elementary motor, sensory or cognitive functions.

The access to brain signals of higher spatio-temporal resolution is possible through electrocorticography (ECOG), whereby an array of electrodes is surgically implanted beneath the skull, typically in the subdural space. The bandwidth of ECOG signals extends well into the γ band (up to 200 Hz) and their spatial resolution is an order of magnitude superior to that of EEG. Our team is developing a wearable analogue of an implantable brain-machine interface that is capable of recording and task-decoding of brain signals with spectral neural content up to 200 Hz. Since ECoG-based neural recording pursued by these research programs mandates surgeries, which are only performed in a small subset of epilepsy patients, they pose a considerable risk and potential complications. Therefore, they are neither appropriate nor justified for the large majority of clinical, science, and consumer/wearable electronics applications. The ability to non-invasively record EEG signals with a spatio-temporal resolution that is reminiscent to that of ECOG would thus be enormously beneficial.

Recent studies have shown that high-density EEG wearable prototypes with inter-electrode pitch smaller than spatial Nyquist rate achieved by standard EEG may lead to modest gains in spatial resolution, and therefore, extract additional useful neural information. Despite the increased sensor density, these systems still employ traditional recording architectures based on single-band (0-30 Hz) amplification and are thus incapable of breaking through the spatio-temporal resolution barrier. Consequently, achieving ECoG-like signal quality by a non-invasive electrophysiological monitoring method remains an open problem. To address the temporal resolution limitation, numerous studies attempted to extract high-frequency information from EEG γ band. However, these claims are largely confounded by strong, high-bandwidth signals of non-cortical origin. Specifically, mechanical artifacts and electromyogram (EMG) from head muscles can easily penetrate the γ band. Pursuing a common philosophy of designing amplifiers covering wider bandwidth, as has been reported by prior studies, would reach the fundamental limit imposed by device physics, and as a consequence, is incapable of achieving the required sensitivity for detection of useful neural information. Therefore, EEG sensing and acquisition technology must be overhauled to dramatically improve the quality of recorded signals. The present example precisely overcomes this fundamental bottleneck, and accomplishes the following objectives:

Aim 1. Development of a novel high-sensitivity artifact-tolerant multiband active electrode (MAE) capable of detecting the entire physiological spectral band.

Aim 2. Development a single-wire array of tightly-connected MAEs immune to mechanical artifacts and capable of non-intrusive wireless connectivity using advanced encryption at the edge.

Figure 6:
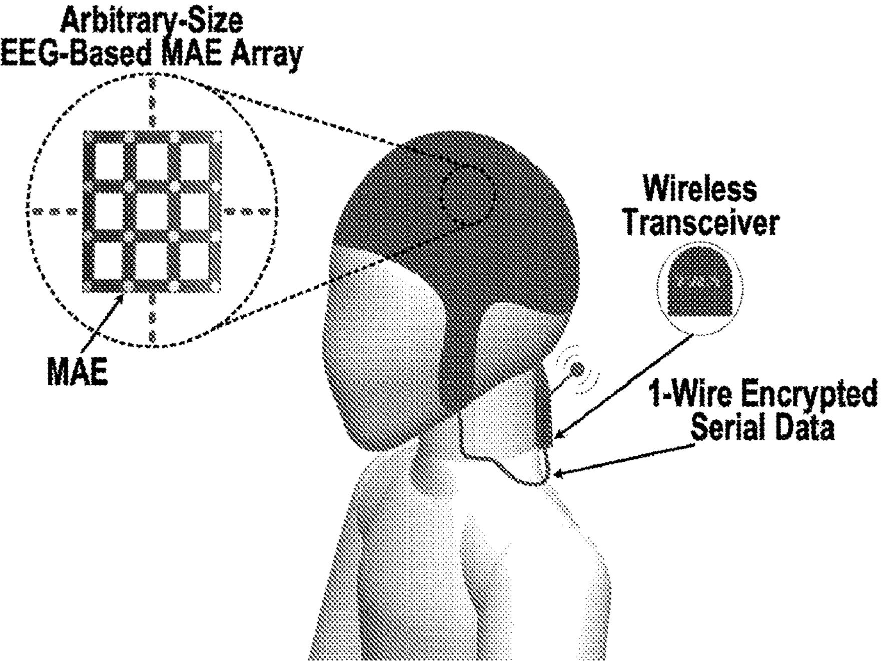
FIG. 6 shows an EEG-base MAE array with a secured single-wire interface.
Figure 7:
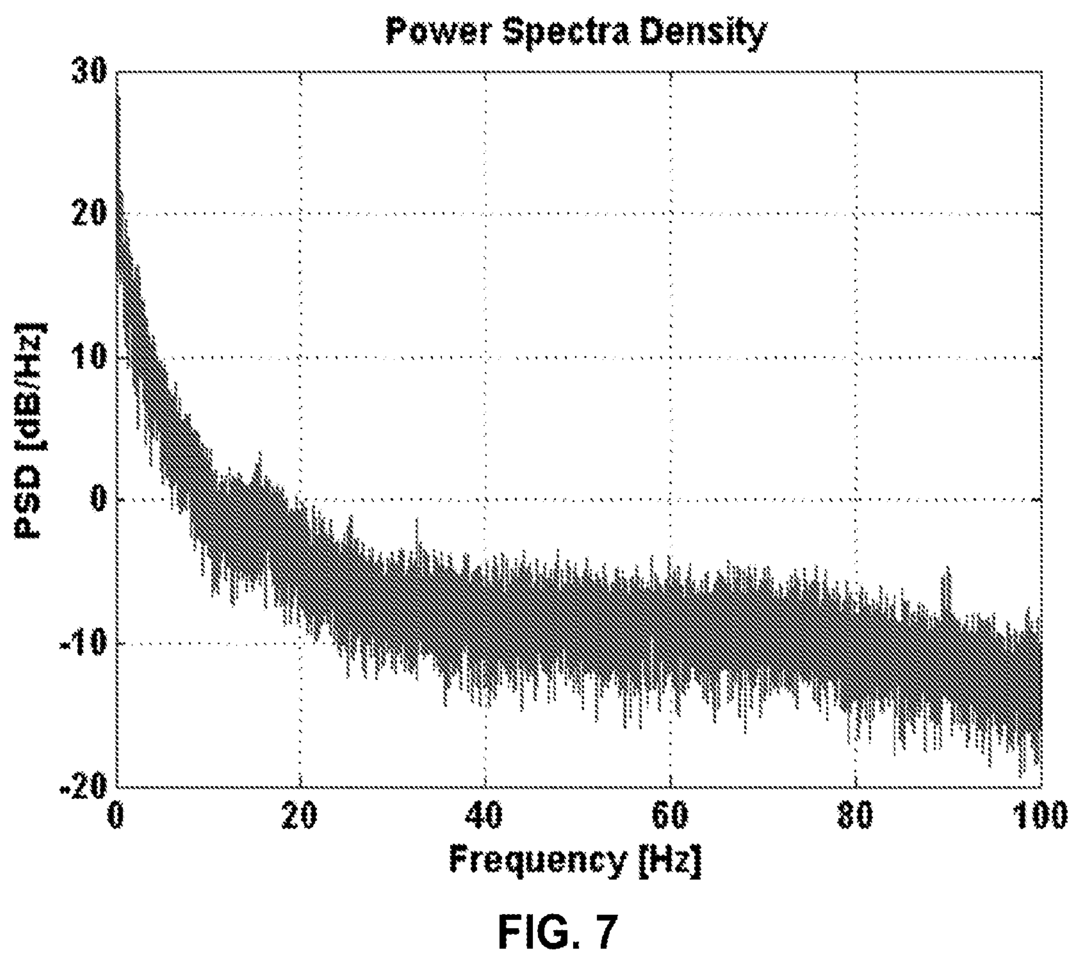
FIG. 7 shows a power spectrum of an EEG signal recorded from the occipital lobe (electrode O1) using a state-of-the-art recording system.

FIG. 6 demonstrates a high-level conceptual schematic of a recording EEG-based MAE array of the present invention. This neural recording array is composed of an extended grid of MAEs connected through an interconnect network. A low-power per-electrode signal acquisition and digitization together with inter-electrode signal processing will realize a high-resolution recording with single-wire output. This serialized data stream may then be encrypted to secure the recording process against malicious attacks. Next, an ultra-low power (ULP) transceiver may establish communication to a remote computing device for brain signal processing. As part of this example, a unique multi-band brain-signal acquisition may be introduced to detect frequency content around and above 200 Hz with extremely high signal-to-noise ratio. In addition, the new one-wire tightly-connected MAE array will significantly improve the portability of the recording system-especially for high-density arrays—by eliminating the need for extended wire-connections between electrode nodes and signal recording module. The present invention may revolutionize non-invasive brain recording and along the way may unfold many new applications.

State of Knowledge

Since EEG is ubiquitously used in research and clinical domains, numerous studies have attempted to circumvent its fundamental spatio-temporal limit and improve the quality of information that can be gleaned from EEG data. In the spatial domain, high-resolution source localization techniques have been employed to statistically infer the location and intensity of putative neural signal sources based on EEG data. However, these methods often employ simple signal propagation models, rely on parameters that are difficult or impossible to measure in living humans, and generally produce non-unique source distributions. More importantly, they cannot be objectively validated since the ground truth (i.e., the number and distribution of neural signal generators) is not known. Alternatively, current source density or spatial deconvolution approaches have been applied to estimate cortical surface potentials; however, they too lack direct validation, as cortical potential distributions are not known even in the simplest of experimental paradigms. To circumvent the temporal resolution limitations, high-impedance bioamplifiers have been developed for the purpose of expanding the bandwidth of EEG signals, possibly into the γ frequency band. The lack of rigorous validation, however, makes the interpretation of these high-frequency EEG components difficult since they can be readily confused with high-frequency biological artifacts, background noise, and acquisition system impairments that are common in EEG.

While the accuracy and precision of the localization of neuronal activity using non-invasive methods is still a matter of debate, recent studies have shown that scalp EEG can indeed sense subcortical signals for frequencies covering a band, which can be reconstructed and located using source imaging techniques. Moreover, prior results contended that EEG electrodes with Nyquist density inter-electrode might be sufficient to extract the maximum possible resolution from EEG signals. However, recent studies establish that acquisition at these spatial Nyquist rates are incapable of achieving resolution mandated in many applications. In fact, a study demonstrating non-standard EEG electrode arrangement has shown that higher density sampling appears to be particularly beneficial under low noise conditions.

In summary, attempts to break through the EEG's spatio-temporal resolution barrier have not been successful, and the utility of EEG as a functional neuroimaging technique thus remains limited. The prevailing paradigm of enhancing the EEG resolution, when neither the source signals nor the transformations that they undergo are known, is not likely to produce any breakthroughs, as can be concluded after decades of research on this subject. Not only does this problem not have a unique solution, but also a potential solution can never be objectively validated and interpreted since the ground truth is not known. Similarly, as previously hinted, the doctrine of using wide-band amplifiers, as has been pursued by the state-of-art works, cannot result in sensitivity needed for non-invasive detection of high frequency neural content. Therefore, a fundamentally novel approach to this problem is needed in order to advance this field beyond the current state.

Figure 8:
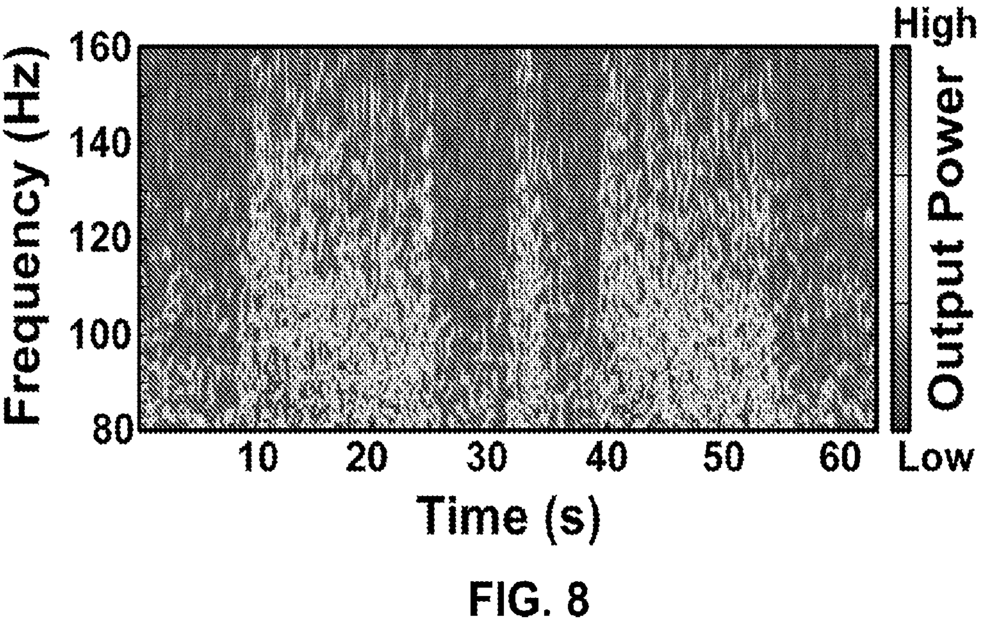
FIG. 8 shows a spectrogram of an ECOG signal exhibiting γ-band power modulations during motor task.

Currently, the only knowledge developed around high-frequency extracellular neural information has been obtained from invasive approaches, such as minimally-invasive ECoG method. Specifically, access to the γ-band of ECOG signals is mostly limited to patients undergoing epilepsy surgery evaluation. Therefore, the amount of evidence regarding how behavioral information is encoded by the brain at this spatio-spectral level is also limited. These higher frequency signals may carry additional information about cognitive, motor, and sensory processes. For example, extracted γ information with rich spectral content has been found to exhibit persistent power modulations during motor tasks, as depicted in FIG. 8, and directly encode movement trajectories. Hence, if ECOG quality signals were as easily accessible as EEG, this would represent an opportunity to study the physiological processes underlying myriad of neurological conditions at a much higher level of spectro-spatial resolution for potential biomarkers or predictors of disease.

A number of other problems affect the overall quality of EEG signals, and similarly, have not been definitively addressed over the past 100 years. EEG recordings are highly susceptible to a variety of biological (e.g., muscle artifacts and eye movement) and non-biological (e.g., movement artifact, dis-connections, or 60 Hz noise) artifacts. A variety of hardware and software filters are typically used to address these problems, but they are not guaranteed to always work. Other means such as blind source separation have also been used, but these approaches are impossible to verify. Furthermore, all of the above approaches may result in the loss of meaningful neurological signal that have spectral overlap with the artifacts. In addition, most of the times, EEG is acquired through the use of conductive gel to lower the impedance of electrode-tissue interface. Gel application and skin cleaning must be done by a trained technician in a medical clinic, which is a long and tedious process, and thus, has very limited applicability for non-medical use. Dry electrodes have been proposed to address this problem. However, while this technology is easier to use and can be more comfortable, it is known that the electrode-tissue impedances for dry electrodes are significantly higher than their gel-based counterparts, and therefore, the EEG quality is degraded.

Significance

The ability to non-invasively record neural signals with an order-of-magnitude improvement in spatio-temporal resolution would fundamentally change the current state of the neuroimaging field. Since the physiological correlates of some of the most important motor, sensory, and cognitive functions are found in the γ band, our ability to design novel scientific experiments and test new hypotheses would be significantly bolstered with a non-invasive system that can capture high-frequency neural signals. Coupled with improved spatial resolution, these technological advances could lead to the development of novel scientific theories in neuroscience, cognitive science, and psychophysics. This is particularly crucial for human studies, where it is generally unethical and risky to deploy invasive recording approaches. Also, the access to ECoG-like signals through non-invasive means could potentially obviate the need for pursuing invasive BCIs. This could, in turn, significantly broaden the adoption of BCI technology for neurorposthetic, neurorehabilitation, and non-clinical applications. Additionally, such a system could potentially improve the diagnosis of epilepsy, sleep disorders, and alterations of consciousness, leading to better clinical outcomes. It could also lead to the development of novel diagnostic tools. Finally, the low-power and user-friendly wireless design coupled with excellent signal quality may inspire the development of novel consumer/wearable electronics applications and products.

A number of previously unresolved challenges in the state-of-the-art EEG recording systems may be addressed by the present invention:

Grand Challenge 1: Detection of neural signals residing at the higher side of the physiological spectrum (e.g., γ band and higher) poses a great hurdle, as the signal power is noticeably less than that of the lower side of the band (e.g., α and β). The current approach to cover the wide frequency range primarily focuses on developing techniques that can improve sensitivity of a wide-band neural acquisition system without exploiting the intrinsic characteristics of brain signal from cerebral cortex.

Grand Challenge 2: EEG acquisition is prone to biological (e.g., chewing or eye movement) and environmental (e.g., mechanical motion) artifacts as well as undesired neural oscillations (e.g., a desynchronization). Since neural signals of interest acquired by conventional recording systems are often indistinguishable from such artifacts or undesired neural activity, false detection becomes inevitable. This issue will be exacerbated at higher frequencies due to the $1/f^m$ ($m \geq 1$) characteristic of EEG spectrum, where the amplitude of the relevant neural signals begins to roll-off sharply. Furthermore, EEG signal processing, typically conducted offline through wireless transmission of massive data, is vulnerable to potential intrusion. This can severely compromise the privacy of highly sensitive information. Safekeeping the neural data in an neural recording system involving wireless transmission is a crucial task, which has not been investigated by prior work.

Grand Challenge 3: EEG recording systems often require operation in the presence of electromagnetically hostile conditions. The ability to suppress the environmental noise (e.g., 50-/60-Hz power-line interference) is critical and heavily depends on the system common-mode rejection. The conventional EEG systems employing shared reference electrodes suffer from common-mode-rejection-ratio (CMRR) degradation due to the systematic mismatch. Given that CMRR degradation becomes even more prominent with increasing number of recording electrodes, any improvement in spatial resolution achieved by high-density configuration of electrodes is accompanied with increased levels of interference. Such contradictory trends are highly undesirable, but they are frequently encountered in existing neural recording systems.

To tackle these grand challenges, the present invention may include the following features:

Feature 1: Considering that different physiological bands exhibit distinct spectral characteristics, an approach may be pursued which decomposes the spectrum into staggered segments of narrow sub-bands and performs amplification and processing of each segment, separately. This narrow-band signal acquisition will boost the sensitivity of sub-bands, especially those residing at the higher side of the spectrum. A degree-of-freedom in performance-tuning provided by sub-banding technique may be leveraged to adaptively adjust the signal-chain characteristics. This will, in turn, prevent the acquisition system from functional deterioration caused by saturation and distortion.

Feature 2: Considering that there is an existing spatio-temporal correlation between neighboring electrodes, a novel non-invasive recording system that leverages this attribute to tackle the artifacts may be used. Specifically, a tightly-connected network of MAEs which facilitates inter-electrode digital communication may lead to a single-wire serialized digital output that is immune to motion artifacts. Furthermore, the possibility of having a single-wire network of MAEs will help disentangle another crucial and unresolved issue, that is, preserving privacy of neural signals being sensed and transmitted. An advanced encryption code (AES) engine may be implemented prior to wireless transmission so as to mitigate the third-party intrusion.

Feature 3: Unlike the conventional fixed referencing method, a unique dual-mode referencing technique may be adopted within the network of MAEs. This technique will enhance the overall system CMRR by eliminating the inherent systematic impedance mismatch. Additionally, it will reduce biological artifacts by providing differential recording only through adjacent electrodes, thereby lowering the magnitude of differential artifacts.

Further investigation and execution of aforementioned ideas will bring forth the possibility of advancing state-of-the-art EEG systems in multiple fronts. The new notion of co-integrating each electrode with its own low-power neural processing integrated system will enable simultaneous acquisition and computation of brain signals with additional benefits. More precisely, the present example may achieve high spatio-temporal resolution and signal-to-noise ratio (SNR) comparable to invasive counterparts such as ECOG. Moreover, narrow-band signal processing within each MAE essentially allows brain-signal acquisition chains with extremely high input impedance (e.g., $\geq 1$ GΩ). This will, in turn, eliminate the need for conductive gels, thereby facilitating the deployment of the neural recording system for out-of-clinic and daily applications such as gaming and autonomous driving.

Aim 1—Develop a Novel High-Sensitivity Artifact-Tolerant MAE

Rational: Considering that the brain signal's power spectrum closely mimics a reciprocal function of frequency, retaining high SNR at higher frequencies becomes challenging due to the impact of intrinsically wide-band device noise and environmental artifacts. To notably improve the sensitivity of constituent amplifier chain within neural acquisition system, the present invention may feature a new approach based on wide-band neural spectral decomposition into narrow sub-bands. To experimentally verify the functionality and performance of this approach, a silicon-based multi-band neural acquisition front-end may be fabricated and characterized.

The MAE Architecture

Most existing EEG recording systems fail to reliably sense, detect, and distinguish the desired brain signal from artifact or environmental noise for frequencies above 30 Hz. More precisely, feature extraction and selection entail severe challenges due to the highly non-linear, non-stationary and artifact-prone nature of EEG signals. To dramatically enhance detection sensitivity of each electrode over a wide bandwidth covering γ bands, a new approach based on the MAE architecture enabling real-time sub-banding of the brain signal sensed by each electrode followed by detection/amplification/digitization of each narrow sub-band may be pursued. This new approach is built upon the foundational observation that narrow-band sensing and amplification provides higher sensitivity than wideband counterpart due to the front-end's noise-floor dependency on bandwidth.

Figure 9:
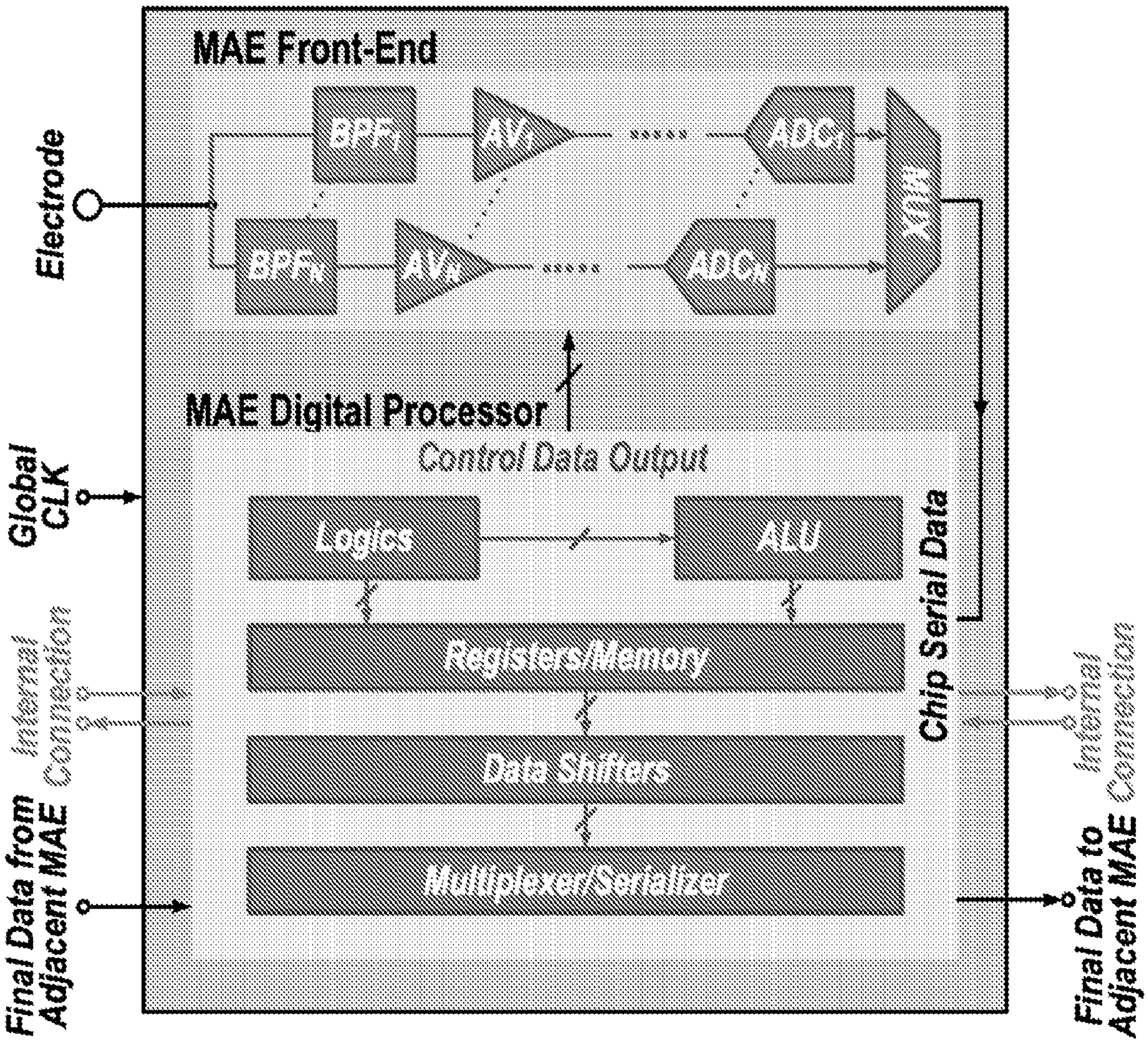
FIG. 9 shows an MAE SoC block diagram of an embodiment of the present invention

FIG. 9 depicts the top-level block diagram of a custom MAE system-on-chip (SoC), which is comprised of two fully integrated core blocks, namely, a ULP MAE front-end (MAE-FE) and a ULP MAE digital processor. The MAE-FE receives the brain signal from the respective EEG electrode and decomposes it into staggered narrow frequency sub-bands. The signal chain associated with each sub-band amplifies, and subsequently, digitizes the signal by a ULP analog-to-digital converter (ADC). The digitized data stream emerging from all sub-band ADCs are finally serialized into one-bit time-multiplexed stream.

The MAE digital processor in FIG. 9, which is comprised of custom arithmetic logic unit (ALU), the logic circuits, memory unit, data shifters, and multiplexers, will process the data, and accordingly, create appropriate control signals for the MAE-FE chain to assist in removing artifacts and preventing saturation. A memory unit is embedded within each MAE to store the processed brain signal and the required control data. Inter-electrode data exchange and serialization may be facilitated via a one-bit digital serial communication among MAEs. This mechanism allows for differential brain signal recording between any two electrodes, estimation of artifacts, and implementation of the dual-mode referencing method.

Multi-Band Brain Acquisition Front-End

Figure 10:
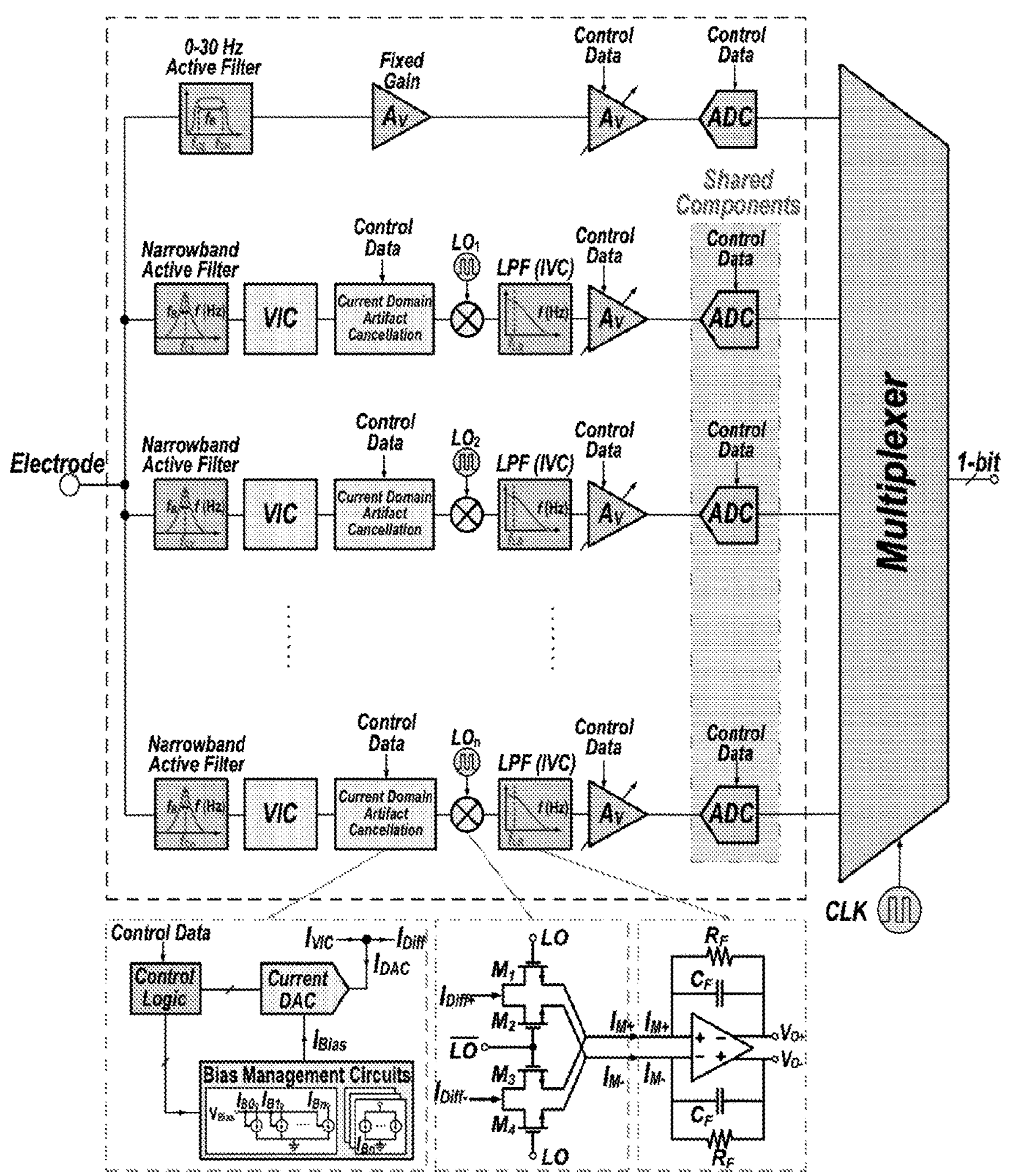
FIG. 10 shows a schematic illustration of a MAE multiband front-end of an embodiment of the present invention.

Operation Principle: FIG. 10 shows the block diagram of the example MAE-FE comprising an array of signal acquisition modules that decomposes the neural spectrum into staggered sub-bands, each with different bandwidth. The first chain is designed to cover low-frequency (0-30 Hz) rhythms falling within the clinical EEG bandwidth, including δ, θ, α, and β. Specifically, it employs a band-pass amplifier with extremely high-input impedance covering the conventional EEG band followed by a variable gain amplifier (VGA) and ADC. In addition, the remaining chains further divide the rest of neural spectrum beyond 30 Hz into small fragments with center frequency of $f_{Ck}$, $1 \leq k \leq n$, where each fragment passes through its own narrowband amplification chain and spectral down-conversion followed by digitization using a ULP high-resolution, low sampling-rate ADC. The digitized data from all constituent ADCs will then be converted to serialized stream of (n+1) $N_{ADC}$-bit long, assuming ADCs with the same resolution, $N_{ADC}$.

Focusing on each individual chain that processes small neural-frequency fragment, a narrow-band BPF is adopted as the first stage, which is realized by an active filter that exhibits high input impedance and in-band gain. A voltage-to-current converter (VIC) then transforms the output voltage of the BPF to a current signal. To better demonstrate the appropriate domain of operation for each block in every signal chain, blue and yellow colors are used to represent the voltage- and current-domain blocks, respectively. The current-domain artifact cancellation module controlled by the built-in MAE digital processor guarantees that artifacts are well-suppressed before reaching the next amplification stages. This is achieved by estimating the artifact magnitude in the MAE digital processor based on the recorded amplitudes received from the far-end MAEs within the recording array.

Following the cancellation of artifacts, a current-mode mixer is used to down-convert the signal to a predefined base-band domain. To preserve the phase of the brain signal (without using in-phase/quadrature mixer structures), the frequency of the local oscillator (LO) within each chain should sustain an offset relative to the center frequency of the respective band. As opposed to having a direct conversion (zero intermediate frequency), a low intermediate frequency (low-IF) architecture is thus used to down-convert the brain signal received by each chain. In this case, the down-converted signal band exhibiting a number of mixing products near DC needs to be extracted and further digitized. At sub-10 Hz frequency range, an LPF implementation offers far less complexity, lower power and minimum area compared to a BPF. Hence, the down-converted signal is filtered using an LPF, which also serves as a current to voltage converter (IVC). The resultant output voltage gets further amplified by a VGA whose gain is well-controlled by the MAE digital processor. Finally, a ULP ADC with high-resolution (e.g., 12 bits) and low sample-rate (e.g., 20 samples/see OSR, where OSR denotes oversampling ratio) digitizes the amplified analog signal in each chain. Neural signals from cerebral cortex have most of their energy concentrated at low frequency, and thus, exhibit strong temporal correlation. On the other hand, sources of noise attributed to the acquisition front-end (e.g., thermal and flicker noise) are uncorrelated. As is widely known, oversampling prior to quantization helps spread the noise power over wider frequency range, leading to significant improvement of SNR at each electrode.

The sub-banding and narrow-band signal processing not only increases the input sensitivity, but can also allow for effective cancellation of biological and environmental artifacts which is a unique feature of the system. The problem of artifact in a non-invasive brain signal recording system is substantial. Biologically-induced motions, mechanical movements, and unwanted neural oscillations (brain signals that are out of the band of interest) are considered to be major sources of undesired fluctuations. Since most of these artifacts, especially unwanted neural oscillations, have narrow-band spectrum with their average power centered at a particular frequency, narrow-band signal amplification and acquisition can be a viable choice to reject the vast majority of these unwanted signals. Based on this notion, each narrowband chain is designed and optimized independently to minimize the presence of in-band unwanted signals and reject out-of-band interference. On the contrary, the conventional wide-band approach treats the neural spectrum as a contiguous band. As a result, local optimization capability of sub-bands is non-existent. This, in turn, translates to over-compensation of signal power at higher side of physiological spectrum, which oftentimes leads to saturation. On the other hand, due to the fact that the signal and artifacts exhibit different spectral characteristics, this approach provides a degree-of-freedom in adjusting the performance based on the signal and noise power profile over each sub-band. This may prevent saturation at lower frequency range, while improving sensitivity and resolution at high frequency.

Moreover, the existence of high-frequency neural content with smaller average power implies the need for high-gain amplifiers with extremely wide dynamic range to detect and process the desired signal in the presence of artifacts. This notion makes the trade-off between system sensitivity and artifact-tolerance a non-trivial issue. Two distinct features of this design systematically address this problem. First, narrowband processing obviates the need for wide dynamic-range amplification. Second, part of the signal processing of each narrowband acquisition chain may be performed in current domain as opposed to the conventional voltage domain, as shown in FIG. 10. Processing in current domain inherently provides higher dynamic range compared to the conventional voltage domain approach, thereby circumventing the saturation problem to a great extent. It is noteworthy that system implementation in advance silicon technologies assumes lower supply voltages (e.g., ≤1 V), which further limits the dynamic range in voltage domain. This observation further justifies the execution of key functions within each narrowband chain in current domain.

Aim 2—Develop an Array of Tightly Connected MAEs

Rationale: To best leverage the existing spatial correlation among neighboring electrodes, a web of tightly connected electrodes forming a cooperative acquisition/processing network may be developed. Such cooperative processing is facilitated by an array of active electrodes with each of those being able to sense, filter, digitize and serialize the brain patterns. In the meantime, cooperative processing and electrode-to-electrode communication significantly improve the spatial resolution by informative neural recording realized by an array of MAEs. Additionally, this cooperative recording scheme enhances system's fault tolerance compared to a conventional centralized front- and bank-end processings, while improving performance and scalability of the entire active electrode array. Furthermore, the ultra-low power brain-signal-acquisition SoC embedded in each active electrode will incorporate functional adaptability that allows each MAE operation to be locally optimized so as to vastly improve the performance of the overall recording system.

Operation Principle

The use of a tightly connected network enables spatial averaging that helps exploit strong spatial correlation between neural signals to further improve signal fidelity. Distributed processing and electrode-to-electrode communication in this design will facilitate real-time spatial averaging without any need for extra software or hardware.

Figure 11:
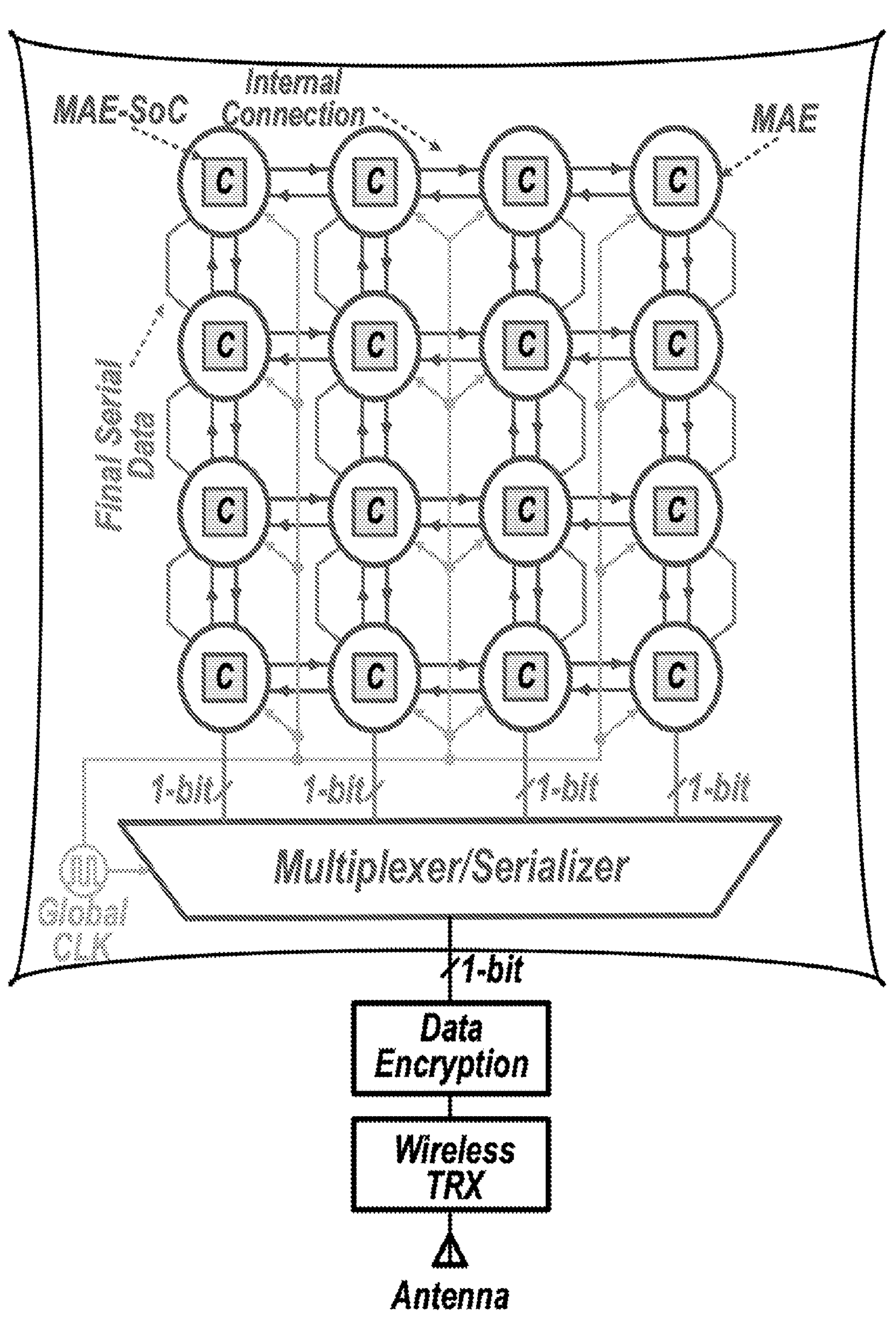
FIG. 11 shows a schematic illustration of an array of tightly connected MAEs.

FIG. 11 shows the schematic of the array of tightly-connected MAEs for a matrix size of N×N (N=4 in this figure). Neural data communication and serialization are carried out in three steps in a pipeline fashion. First, following neural acquisition by each MAE, bi-directional communication (indicated by blue lines) between adjacent electrodes facilitate the content exchange among all MAEs. The whole process of content exchange will be complete in (2N—2) clock cycles. At end of this step, each MAE will collect all the data from all MAEs, perform local computation intended for spatial averaging and artifact cancellation, and produce its serialized data stream. Next, this data stream will propagate from one MAE to another within the same column using a pipelined mechanism to improve throughput. Finally, all one-bit data emerging from MAEs in the same column will be further serialized by an N-to-1 serializer to produce a single-wire output. This process will be complete in (n+1) $N_{ADC}$×N clock cycles. To synchronize multi-step operations among all composing MAEs, a global clock distribution network, shown by the light gray lines in the figure, is envisioned.

The single-wire serialization approach improves portability and flexibility of the recording system, significantly reduces its size and enhances its aesthetic feature, and lessens the system vulnerability to mechanical artifacts induced by physical movements. Existing EEG recording systems require huge number of long interconnects bundled together, which are vulnerable to interference and mechanical artifact. The notion of having a tightly connected array of active electrodes eliminates the need for these bulky and long interconnects, thereby making the system resilient to artifact and interference. Alternatively, the tightly connected network in FIG. 8 leverages existing spatial correlation between electrodes to conduct two major performance-improving tasks, i.e., (1) detection and removal of motion artifacts, and (2) increasing the SNR. The SNR improvement stems from the fact that MAE array structure processes and coherently combines brain signals, whereas it treats the system noise in a non-coherent fashion. All these vantage features expand the application domain of the non-invasive recording to uncharted territory covering wearable mind-controlled devices that far exceeds the neural repair applications.

Encryption at the Edge

The neural decoding and cognitive interpretation will be handled by a separate processing unit located at a short distance from the user. While this short distance makes it less likely that a third-party be able to orchestrate malicious attack, however, the possibility of accessing to an extremely private and sensitive brain information of an individual opens up a whole new domain of vulnerability. This indicates that, although unlikely, the data interrogation should be avoided and the serialized data be protected. The data may be encrypted using the advanced encryption standard (AES), which is a widely adopted security standard of data encryption for emerging wireless networks and Internet of Things (IoT) applications. Three strategies for AES encryption implementation can be conceived, namely, software, field-programmable field array (FPGA), or application-specific integrated circuit (ASIC). Preliminary simulations show that for data rates varying from 1 kbps to 1 Mbps, the average spectral power varies from 1.0-2.0 mW/Hz to 2.5-5.0 mW/Hz for software, 50-100 μW/Hz to 15-250 μW/Hz for FPGA, and 2-4 μW/Hz to 8-10 μW/Hz for ASIC implementation. While ASIC approach offers significant area and power saving, it involves design and implementation of a sophisticated integrated circuit in silicon, which falls beyond the scope of this work. A low-power AES-128 encryption engine in FPGA may be implemented. The FPGA implementation lays the groundwork for future development of this AES engine involving custom integrated circuit design. An off-the-shelf Bluetooth low-energy wireless radio will be employed to transmit this encrypted data to an off-site processing unit, as indicated in black in FIG. 11.

Figure 12A:
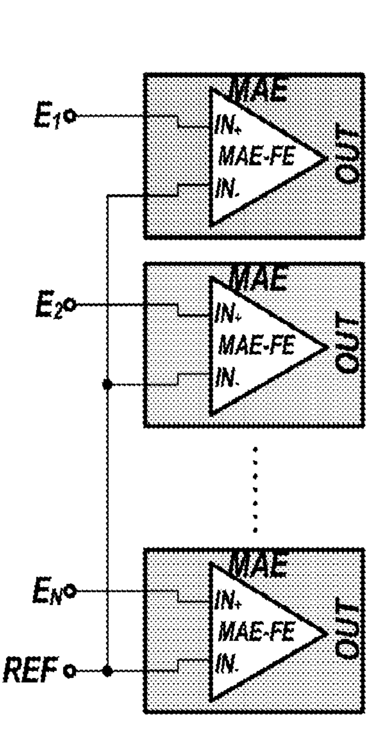
FIG. 12A shows a schematic illustration of fixed referencing.

Electrode Referencing Scheme:

EEG signals are conventionally acquired by recording the absolute value of the signal on each electrode relative to a shared electrode. Commonly known as fixed referencing and depicted in FIG. 12A, this topology is prone to sensitivity degradation due to mismatches induced by process variation as well as common-mode noise-most notably, power-line noise at 60 Hz, introduced the common-average referencing (CAR) technique at the recording front-end to overcome the shortcomings of fixed referencing method. However, this approach suffers from signal contamination that may arise when a single channel senses signals with large amplitude or a broken channel is encountered.

Figure 12B:
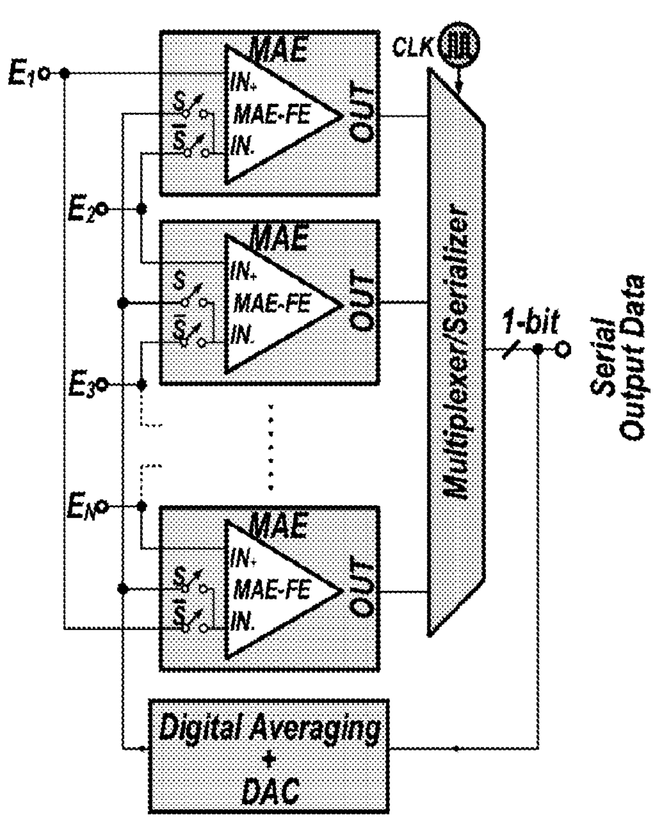
FIG. 12B shows a schematic illustration of dual-mode referencing.

Two original methods which may alleviate the systematic impedance imbalance of conventional fixed-referencing configurations are: (i) feedback-based average referencing, and (ii) dynamic referencing. FIG. 12B shows the schematic of a referencing scheme which employs dual-mode-switching. The network of MAEs is designed in a way that can selectively accommodate both methods. Based on FIG. 12B, if mode-select control signal S is logic high (S='1'), the network will use the average referencing technique, and if S='0', the circuit will be configured to adopt the dynamic referencing mechanism.

In the average referencing mode, the network connection between MAEs makes it feasible to incorporate a feedback loop that can track and correct the value of the reference voltage in the presence of undesired impairments such as common-mode noise and offset voltages. Prior to recording the brain signal, all electrodes are connected to the ground voltage. The calibration system will then read the output signals (containing the amplified versions of offset voltages and common-mode noise), perform averaging, and determine the optimum voltage of the reference node to minimize the effects of mismatches and common-mode interference components. The average referencing technique mitigates deleterious effects of common-mode noise on the system performance compared to the fixed reference recording scheme, and prevents the common—to differential-mode signal conversion.

Figure 13A:
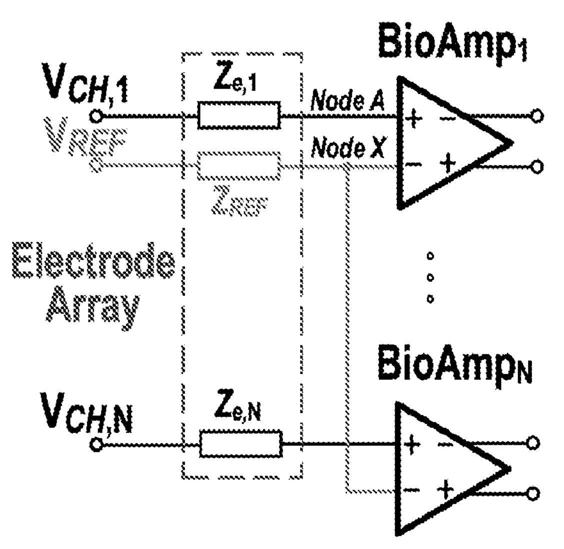
FIG. 13A shows a schematic illustration of a conventional N-channel biosignal acquisition front-end with shared reference.
Figure 13B:
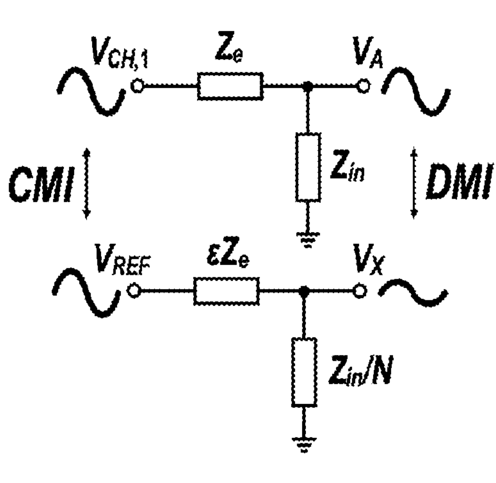
FIG. 13B shows a schematic illustration of a simplified electrical model of the input interface. $Z_{e,k}$ for $1 \le k \le N$ denotes the electrode impedance. $Z_{REF}$ and $Z_{in}$ represent reference electrode and amplifier's input impedance, respectively. $\epsilon$ models the mismatch between reference and recording electrode impedances.

The dynamic referencing mode offers a clear advantage inherent to this network of tightly connected MAEs. The connection sequence among MAEs is designated in such a way that allows us to establish differential recording, while eliminating the need for shared reference. More specifically, each electrode $E_k$ is connected to input terminals of two MAEs, $MAE_{k-1}$ and $MAE_k$, where $1 \leq k \pmod{N} \leq N$. The shared-reference scheme is inherently a source of systematic impedance imbalance, which, together with electrode impedance mismatch, gives rise to unequal potential divider effect (FIGS. 13A-B). Therefore, the impedance mismatch at the interface between electrodes and MAEs is completely mitigated in this mode, resulting in a higher CMRR and improved resilience against common-mode interference.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A multiband active electrode (MAE) for electroencephalography (EEG), the MAE comprising a wide band filter for a sub-band with a frequency range from 0-30 Hz, and a plurality of narrow-band filters for sub-bands with frequencies above 30 Hz, wherein the MAE is configured to split a detected EEG signal into a plurality of sub-bands, and separately amplify and process each of the sub-bands, wherein at least one of the sub-bands has a frequency above 30 Hz.

2. The MAE of claim 1, wherein the narrow-band filters each have a bandwidth of about 5-10 Hz.

3. The MAE of claim 1, wherein the MAE is configured to digitize the processed sub-bands to generate a serialized data stream.

4. A multiband active electrode (MAE) for electroencephalography (EEG), the MAE comprising a front-end processor and a digital processor, wherein the MAE is configured to split a detected EEG signal into a plurality of sub-bands, and separately amplify and process each of the sub-bands, wherein the front-end processor is configured to decompose the detected EEG signal into the plurality of sub-bands, amplify each sub-band, digitize each sub-band into a data stream, and serialize the data streams into a time-multiplexed data stream.

5. The MAE of claim 4, wherein the digital processor is configured to cancel artifacts from the digitized data streams.

6. A multiband active electrode (MAE) for electroencephalography (EEG), wherein the MAE is configured to split a detected EEG signal into a plurality of sub-bands, and separately amplify and process each of the sub-bands, wherein the MAE is further configured to cancel artifacts via communicating with neighboring MAEs.

* * * * *